(12) United States Patent
Roe et al.

(10) Patent No.: US 10,349,800 B2
(45) Date of Patent: Jul. 16, 2019

(54) BONDED LAMINATE CLEANING IMPLEMENT

(71) Applicant: The Procter & Gamble Company, Cincinnati, OH (US)

(72) Inventors: Donald Carroll Roe, West Chester, OH (US); Jill Marlene Orr, Liberty Township, OH (US); John Joseph Curro, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 998 days.

(21) Appl. No.: 14/307,924

(22) Filed: Jun. 18, 2014

(65) Prior Publication Data

US 2014/0366294 A1 Dec. 18, 2014

Related U.S. Application Data

(60) Provisional application No. 61/836,209, filed on Jun. 18, 2013.

(51) Int. Cl.

| | |
|---|---|
| *A47L 13/17* | (2006.01) |
| *A61F 13/15* | (2006.01) |
| *B32B 5/26* | (2006.01) |
| *B32B 5/02* | (2006.01) |
| *B32B 5/24* | (2006.01) |
| *B32B 3/12* | (2006.01) |
| *B32B 3/26* | (2006.01) |
| *B32B 3/30* | (2006.01) |

(52) U.S. Cl.
CPC ............. *A47L 13/17* (2013.01); *A61F 13/15* (2013.01); *B32B 3/12* (2013.01); *B32B 3/266* (2013.01); *B32B 3/30* (2013.01); *B32B 5/022* (2013.01); *B32B 5/245* (2013.01); *B32B 5/26* (2013.01); *B32B 2262/0253* (2013.01); *B32B 2262/0276* (2013.01); *B32B 2262/062* (2013.01); *B32B 2266/06* (2013.01); *B32B 2307/7265* (2013.01); *B32B 2432/00* (2013.01)

(58) Field of Classification Search
CPC ............. A47L 13/17; A61F 13/15; B32B 5/26
See application file for complete search history.

(56) References Cited

U.S. PATENT DOCUMENTS

| | | | | |
|---|---|---|---|---|
| 5,108,642 | A | * | 4/1992 | Aszman ................... A47L 13/17 510/199 |
| 2002/0155772 | A1 | * | 10/2002 | Wong ........................ B08B 1/00 442/123 |
| 2006/0052269 | A1 | | 3/2006 | Panandiker et al. |

(Continued)

FOREIGN PATENT DOCUMENTS

FR 2 822 045 A1 9/2002

OTHER PUBLICATIONS

U.S. Appl. No. 14/307,892, filed Jun. 18, 2014, Roe, et al.

(Continued)

*Primary Examiner* — Randall E Chin
(74) *Attorney, Agent, or Firm* — C. Brant Cook

(57) ABSTRACT

A laminate cleaning implement. The laminate cleaning implement has a backing sheet, a substrate, and a facing sheet. The backing sheet and the facing sheet are connected at a plurality of discrete bonding points to form a coherent laminate structure and the substrate is disposed between the backing sheet and the facing sheet.

24 Claims, 2 Drawing Sheets

(56) References Cited

U.S. PATENT DOCUMENTS

| | | | | |
|---|---|---|---|---|
| 2006/0159729 A1* | 7/2006 | Helfman | ............... | A47L 13/17 |
| | | | | 424/443 |
| 2006/0247585 A1* | 11/2006 | Kelly | ................... | A45D 34/04 |
| | | | | 604/290 |
| 2010/0173817 A1* | 7/2010 | Glenn, Jr. | ............... | A61K 8/11 |
| | | | | 510/120 |
| 2010/0306937 A1* | 12/2010 | Konishi | ............... | A47K 11/10 |
| | | | | 15/104.93 |

OTHER PUBLICATIONS

PCT International Search Report dated Nov. 3, 2014—4 pages.
All Office Actions in U.S. Appl. Nos. 14/307,892; and U.S. Appl. No. 14/307,924.

* cited by examiner

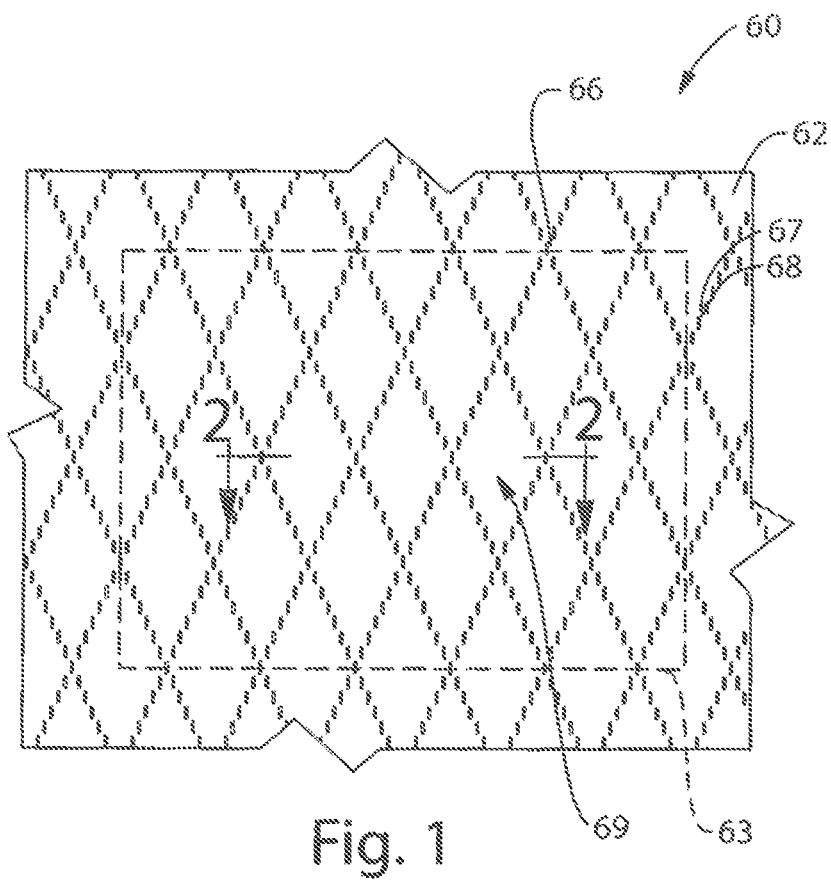
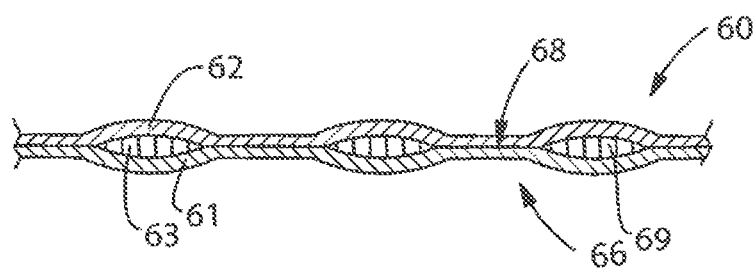
Fig. 1
Fig. 2

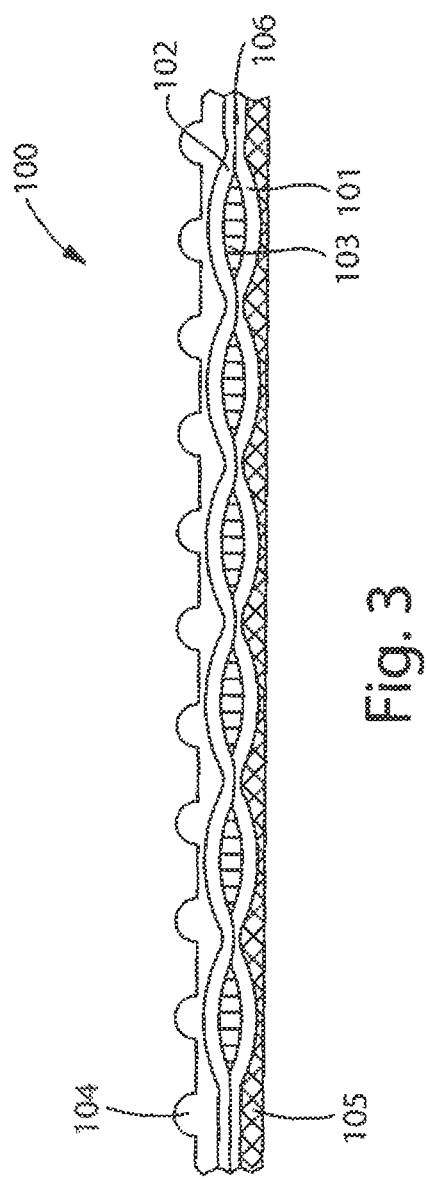

BONDED LAMINATE CLEANING IMPLEMENT

FIELD OF THE INVENTION

The present invention is generally relates to a multilayer laminate cleaning implement, and more particularly to a multilayer laminate wherein at least one layer is a substrate.

BACKGROUND OF THE INVENTION

Many cleaning products, including shampoo, body wash, dentifrice, and hard surface cleaners, are sold containing water. The water in the formula adds to the weight of the products and translates into greater shipping and storage costs. Additionally, these types of products also have disadvantages in terms of packaging, storage, transportation, and convenience of use.

In order to use many cleaning products, the user must dispense the cleaning product from a bottle or other closed vessel onto the target surface, and then utilizing a sponge, towel, brush, or other implement distribute the product on the surface and, if desired, absorb any excess product, potentially with another implement or substrate.

This practice is widely used, but is often inefficient. For instance, when a caregiver washes a pet she must wet the pet, open the shampoo, put shampoo on the pet, rub the shampoo into the pet's coat, and then rinse the pet. This process must be repeated multiple times to clean the entire pet and it can be particularly difficult to adequately clean the legs, abdomen, and buttocks of the animal. Furthermore, if the caregiver is using a bottled shampoo, she must repeatedly handle the shampoo container with wet, slippery, soapy hands to dispense shampoo. All of this must be done while keeping the pet in the washing area. Since washing a pet can be difficult, the user may rush and not thoroughly clean the pet.

It would be desirable to have a cleaning product combined with an implement to make cleaning more efficient. However, making these combination products can be cumbersome. For instance, some products have a cleaning product sprayed onto an outer surface of an assembled cleaning implement and a drying step is required before the cleaning product can be packaged. Other combination products have a cleaning composition residing within a cleaning implement, however, processing steps, such as adding texture to a surface of the cleaning implement, must be completed before the cleaning composition is combined the other parts of the cleaning implement.

It would also be desirable for such a cleaning product to capture the removed soil from the animate and/or inanimate surfaces being cleaned.

Accordingly, there is a need for a laminate cleaning implement comprising a substrate that provides cleaning benefits, soil capture benefits, streamlines the cleaning process, and allows for a simplified manufacturing method. The cleaning implement can eliminate the need to carry and store cumbersome bottles, bars, jars, tubes, and other forms of clutter associated with cleaning products. Additionally, the cleaning implement can be designed to provide superior cleaning to the intended surface and soil removal from the intended surface. Furthermore, if the laminate cleaning implement is disposable it can be more sanitary than using a sponge, washcloth, or other cleaning implement intended for extensive reuse, because such implements can develop bacterial growth, unpleasant odors, and other undesirable characteristics related to repeated use.

SUMMARY OF THE INVENTION

A laminate cleaning implement comprising: (a) a backing sheet; (b) a substrate comprising an active agent wherein upon exposure to conditions of intended use the active agent is released; and (c) a facing sheet; wherein the backing sheet and the facing sheet are connected at a plurality of discrete bonding points to form a coherent laminate structure and wherein the substrate is disposed between the backing sheet and the facing sheet.

A laminate cleaning implement comprising: (a) a textured sheet; (b) a bonded laminate comprising: (i) a backing sheet; (ii) a substrate comprising an active agent wherein upon exposure to conditions of intended use the active agent is released; and a facing sheet; wherein the backing sheet and the facing sheet are connected at a plurality of discrete bonding points to form a coherent laminate and wherein the substrate is disposed between the backing sheet and the facing sheet.

In still another example of the present invention, a laminate cleaning implement comprising (a) a facing sheet and (b) a substrate comprising an active agent wherein upon exposure to conditions of intended use the active agent is released, wherein the facing sheet and substrate are connected at a plurality of discrete bonding points to form a coherent laminate, and optionally, wherein a composition, such as a composition comprising a soil capture agent, is present on the facing sheet, is provided.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 1 is a schematic representation of a top view of a portion of a bonded laminate web suitable for use in a cleaning implement of the present invention;

FIG. 2 is a schematic representation of an enlarged cross-sectional view of section 1-1 of FIG. 1; and FIG. 3 is a schematic representation of a cross-sectional view of a portion of a laminate cleaning implement of the present invention.

DETAILED DESCRIPTION OF THE INVENTION

The laminate cleaning implement can comprise a facing sheet, a backing sheet, and a substrate disposed between the facing sheet and the backing sheet that can be used to clean and/or capture soil from any surface, hard or soft. The substrate can comprise an active agent that can be used to clean any surface including hard surfaces (i.e., kitchen countertops, bath tubs, toilets, toilet bowls, sinks, floors, walls, teeth, cars, windows, mirrors, dishes), soft surfaces (i.e., fabric, hair including human hair and pet hair, skin, carpet, crops, plants), and combinations thereof. Soon after the cleaning implement is exposed to conditions of intended use, the substrate becomes dispersible and the active agent can be distributed across the surface to be cleaned or treated.

In one example, the facing sheet, the backing sheet, and the substrate are joined by bonding. During the bonding process the facing sheet can bind directly to the backing sheet at the bonding points, and the substrate, which is disposed between the sheets, can be "squeezed" or otherwise substantially displaced out of the plurality of bonding points.

Bonding the facing sheet, the backing sheet, and the substrate can help simplify manufacturing as well as improve performance of the cleaning implement. In one example, the substrate can be a solid, before it is exposed to conditions of intended use and combining a solid substrate with the facing and backing sheets can simplify manufacturing by eliminating the drying step. Furthermore, the substrate can comprise enough cleaning composition to clean a large area, if desired. This allows the laminate cleaning implement to have a wide variety of uses including cleaning large pets, cars, hard surfaces, or humans, with only one cleaning implement.

In order to use the laminate cleaning implement, the user exposes the cleaning implement to conditions of intended use. As used herein, "conditions of intended use" means the temperature, physical, chemical, and/or mechanical conditions that a substrate is exposed to when it is used as a cleaning implement.

In one example, the substrate can include an active agent. As used herein, "active agent" or "active" means an additive that produces an intended effect in an environment external to a substrate, such as when the substrate is exposed to conditions of intended use. In one example, an active agent treats a surface, such as a hard surface and/or a soft surface. In another example, an active agent creates a chemical reaction (i.e., foaming, fizzing, coloring, warming, cooling, lathering, disinfecting). In yet another example, an active agent treats an environment (i.e., deodorizes, adsorbs odor, purifies, perfumes air). In yet another example, the active agent binds a target substance, such as soil Active agents may be any suitable additive that produces an intended effect under intended use conditions of the substrate. For example, the active agent may be selected from the group consisting of: personal cleansing and/or conditioning agents such as hair care agents including shampoo agents, skin cleansing agents, hair conditioning agents, hair coloring agents, bleaching agents, skin care agents, surfactants, moisturizers, protectants, barrier materials, smoothing agents, lubricants, fabric care agents, fabric softening agents, fabric care stain removal agents, soil release agents, soil-capture or binding agents, dispersing agents, dishwashing agents (for hand dishwashing and/or automatic dishwashing machine applications), hard surface cleansing agents, bleaching agents, carpet care agents, make-up removal agents, deposition aids, perfumes, odor absorbing agents, tooth care agents for humans and pets, ear care agents for humans and pets, and mixtures thereof.

One or more classes of chemicals may be useful for one or more of the active agents. For example, surfactants may be used for any number of the active agents. Likewise, bleaching agents may be used for fabric care, hard surface cleaning, dishwashing and even teeth whitening. Therefore, one of ordinary skill in the art will appreciate that the active agents will be selected based upon the desired intended use of the cleaning implement made therefrom.

In another example, a second active agent can be deposited on or incorporated into the facing sheet and/or the backing sheet.

As used herein, the term "aperture", refers to a hole. The apertures can either be punched cleanly through the facing sheet, the backing sheet, and/or the substrate so that the material surrounding the aperture lies in the same plane as the facing sheet, backing sheet, or substrate prior to the formation of the aperture (a "two dimensional" aperture), or holes formed in which at least some of the material surrounding the opening is pushed out of the plane of the facing sheet, backing sheet, and/or substrate. In the latter case, the apertures may resemble a protrusion or depression with an aperture therein, and may be referred to herein as a "three dimensional" aperture, a subset of apertures. The apertures can be created by any suitable means including die cut holes, slitting and stretching the sheets and/or substrate, and combinations thereof. The laminate cleaning implement can comprise one or more sheets comprising apertures.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, "discrete" means distinct or unconnected.

As used herein, "disposable" refers to an implement that is disposed or discarded after a limited number of usage events. In one example, the disposable implement is used five or fewer times, in another example three or fewer times, in another example two or fewer times, and in another example the disposable implement is used only one time.

As used herein, "g/use" refers to grams per use. This is the unit used for rate of consumption and the method for measuring and/or calculating it is described in the Consumption rate test herein.

As used herein, "glove" refers to a covering for the hand having separate sections for each finger.

As used herein, "indicia" provides information to a potential user or user of the systems, liquid medication (e.g. the active contained therein) and sachets. The indicia can comprise many forms and present the information in many ways and in many types of media. Non-limiting examples of types of indicia include alpha-numeric indicia, pictures, drawings, illustrations, photographs, computer-produced images, colors, sounds, textures, shapes, symbols, letters, numbers, and combinations thereof.

As used herein, "mitt" refers to a covering for the hand that is partially or wholly unseparated and that may include space for the thumb in the main enclosure or may provide space for the thumb in a separate enclosure for the thumb or may not include a thumb enclosure at all. This term is also applicable to an implement that covers only one or more digits of a user, such as in the case of a "finger mitt".

While the terms "glove" and "mitt" have been defined with respect to the human hand, similar structures could be utilized to cover or enclose other elements of human anatomy, such as foot coverings, or other items for which coverings of a particular shape are preferred.

As used herein, "joined" refers to configurations in which a first element is secured to a second element. Joined also includes configurations in which the first element is indirectly secured to the second element.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than 5 weight percent and more typically 2 weight percent.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One preferred capillary channel fiber is T-401, designated as 4DG fiber available from Fiber Innovation Technologies, Johnson City, Term. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not have randomly oriented fibers. Nonwoven web or fabrics can be formed from many known processes, such as, for example, air laying processes, meltblowing processes, spunbonding processes, hydroentangling processes, spunlacing processes, and bonded carded web processes. Also, multi-layer webs, such as spunbond-meltblown-spunbond webs and the like made by multiple beam spunbond processes, can be used. Fibers can be bicomponent, multicomponent, multiconstituent, and the like, as known in the art. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 5 to 500 g/m².

As used herein, "on-the-hand implement" refers to a covering for the hand or portion of the hand such as a finger, thumb, or palm.

As used herein, "pet" means dogs, cats, small mammals such as gerbils, hamsters, chinchillas, rats, rabbits, guinea pigs, and ferrets, and/or other domesticated animals.

As used herein, "permanently joined" refers to configurations in which a first element is secured to a second element such that the elements generally cannot be separated from one another without at least partially destroying one or both of the elements.

As used herein, the term "polymer" is used in its conventional meaning, and generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries. In general, any of the known polymer types can be used, for example, polyolefinic polymers such as polypropylene or polyethylene can be used either as monocomponent fibers or bicomponent fibers. Other polymers such as PVA, PET polyesters, metallocene catalyst elastomers, nylon and blends thereof can be used. Any or all of the polymers can be cross-linked if desired.

As used herein, "releasably joined" refers to configurations in which a first element is secured to a second element, such that the first element and the second element can be separated with no or minimal damage to the first and second elements.

As used herein, "SELF" or "SELFing", refer to Procter & Gamble technology in which SELF stands for Structural Elastic Like Film. While the process was originally developed for deforming polymer film to have beneficial structural characteristics, it has been found that the SELFing process can be used to produce beneficial structures in other materials, such as fibrous materials. Processes, apparatus, and patterns produced via SELF are illustrated and described in U.S. Pat. Nos. 5,518,801; 5,691,035; 5,723,087; 5,891,544; 5,916,663; 6,027,483; and, 7,527,615.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, "tuft", refers to a particular type of protrusion that may be formed in a nonwoven web. Tufts typically have a tunnel-like configuration, and in some cases may be open at one or both of their ends.

As used herein, "water-soluble material" means a material that is miscible in water with sufficient time and/or agitation. In other words, a material that is capable of forming a stable (does not separate for greater than 5 minutes after forming the homogeneous solution) homogeneous solution with water at ambient conditions.

As used herein, "usage event" refers to one five minute cycle of the Consumption rate test below.

As used herein, "ambient conditions" means 73° F.±4° F. (about 23° C.±2.2° C.) and a relative humidity of 50%±10%.

As used herein, the articles "a" and "an" when used herein, for example, "an anionic surfactant" or "a fiber" is understood to mean one or more of the material that is claimed or described.

The laminate cleaning implement can comprise any number of sheets. In one example, the laminate cleaning implement can comprise a facing sheet, a backing sheet, and a substrate disposed between the facing sheet and the backing sheet. After the cleaning implement is exposed to conditions of intended use, at least a portion of the substrate becomes dispersible and the substrate and/or active agent can be distributed across the surface to be cleaned or treated.

The facing sheet, the backing sheet, and the substrate can be processed into a coherent laminate by any suitable joining means. Non-limiting examples of suitable joining means can include bonding, ultrasonic welding, thermal calendaring, mechanical means, thermomechanical means, adhesives, sewing, and combinations thereof.

In one example, the laminate cleaning implement can be formed without the use of adhesives or sewing. This can simplify processing, ultimately lowering the cost of the laminate web. Furthermore, eliminating adhesives can make the laminate cleaning implement more flexible and softer.

In a preferred example, the facing sheet, the backing sheet, and the substrate are joined by bonding. Non-limiting examples of bonding processes can include thermal bonding, pressure bonding, ultrasonic bonding, and combinations thereof. In one example, during the bonding process the facing sheet can bind directly to the backing sheet at the bonding points, and the substrate, which is disposed between the sheets, can be "squeezed" or otherwise substantially displaced out of the plurality of bonding points.

In another example, one sheet, for instance the backing sheet, is water impermeable. In another example, the laminate cleaning implement further comprises an impermeable substrate. The water impermeable substrate and/or water impermeable sheet can prevent the user's hand from getting wet and/or coming into contact with the cleaning composition during use. In one example, the water impermeable substrate and/or water impermeable sheet is adapted to be held by the user during cleaning. In another example, the impermeable substrate or impermeable sheet can be used to distribute the cleaning composition across the surface to be cleaned.

In one example, the facing sheet and/or the backing sheet can comprise textured portions. In another example, an additional textured sheet is added to the laminate cleaning implement which comprises the textured portions. In one example, the additional textured sheet is added on top of the facing sheet.

The textured portion can increase the effective available surface area and therefore when the laminate is exposed to conditions of intended use, such as water or another aqueous solution, the water or solution can more quickly penetrate through the facing sheet and come into contact with the substrate.

Non-limiting examples of textured portions can include protrusions, depressions, apertures, embossing, debossing, and combinations thereof. The textured portions can increase the surface area of the laminate cleaning implement, which can increase the rate the substrate becomes dispersible after being in contact with conditions of intended use.

The textured portions can also assist in cleaning. For instance, the textured portions can provide additional abrasion which can be helpful in removing dirt and stains, especially tightly adhered stains, from a surface. The textured portions can also be customized depending on the desired use for the cleaning implement.

In one example, the cleaning implement can be used to clean a pet's coat and the textured portions can help penetrate the coat, which helps to disperse the substrate and any active agents throughout the coat as well as remove debris including hair and massage the pet's skin. In one example, the cleaning implement is a mitt or glove and the textured portions are on the portion of the glove that covers the user's fingers.

The textured portions can be randomly arranged or arranged in a repetitive pattern of some form on either side of the laminate cleaning implement. In another example, the textured portions are only located on a certain part of the cleaning implement, for instance portion(s) that are involved in scrubbing and/or the portion(s) of the cleaning implement that comprises the substrate.

In one example, the textured portions can be made by SELFing, which can be done before the cleaning implement is assembled. SELFing creates protrusions, referred to herein as tufts. In one example, the tufts can protrude outwardly from the facing sheet or backing sheet. In one example, the additional textured sheet is a sheet comprising tufts.

In another example, the laminate cleaning implement further comprises a rigid backing layer that can provide additional stiffness to the cleaning implement, which can make it easier to use.

The facing sheet and backing sheet can be any suitable material and the material can be selected based on the surface to be cleaned. For instance, if the laminate cleaning implement is intended to be used to clean something delicate or sensitive, such as human skin, then a material that feels softer can be selected for the precursor web. However, if the cleaning implement is intended to be used to clean a more robust surface, then a material that feels stiffer or rougher can be selected. The softness or stiffness of the sheets can be changed depending on the basis weight of the constituent material, the size of the denier fibers, and the strength or stiffness of the constituent material.

In certain examples, the sheets can be nonwovens (i.e. a natural or synthetic nonwovens including fibrous and non-fibrous nonwovens), wovens, films (e.g. a formed film), sponges (e.g. a natural or synthetic sponge), polymeric netted meshes (i.e. a "scrim"), batting, spunbound, spunlace, hydroentangled, carded, needlepunch, or any other suitable material. In one example, the sheets can be fibrous nonwovens. In another example, one or both sheets are water-stable but water permeable.

In one example, the backing sheet is the same as the facing sheet. In another example, the backing sheet is a different material than the facing sheet. For example, the backing sheet can be stiffer than the facing sheet thereby making the laminate cleaning implement more rigid. In another example, each side of the cleaning implement can be used for a different purpose. For instance, the first side comprising the facing sheet can be used for a first purpose, such as distributing a first active agent, such as a shampoo, soap, body wash, or dish cleaner, across the surface to be cleaned and the second side comprising the backing sheet can be used for a second purpose, such as drying the surface and/or spread a second active agent, such as a conditioner or drying agent, across the surface.

The substrate can be any composition that can comprise an active agent, can become dispersible upon conditions of intended use, and can be subjected to a mechanical deformation process. Non-limiting examples of substrates can include open cell foams, as described herein and in U.S. Pat. No. 8,268,764 and U.S. patent application Ser. No. 12/361,634, now U.S. Pat. No. 8,765,170; Ser. No. 12/633,415, now U.S. Pat. No. 8,415,287; and Ser. No. 13/440,475, abandoned Dec. 16, 2015; dissolvable filament substrates, as described herein and in U.S. patent application Ser. No. 13/229,791, Publication No. 2012/0052036 A1 now pending; Ser. No. 13/229,818, Publication No. 2012/0027838 A1 now pending; and Ser. No. 13/229,845, now U.S. Pat. No. 9,175,250; compliant doughs, as described herein and in U.S. Pat. No. 6,491,928 and U.S. patent application Ser. No. 13/438,918, now U.S. Pat. No. 9,592,181; films, fibers including nonwoven fibers, webs including nonwoven webs, closed cell foams, pastes, particles, flakes, powders, and combinations thereof. Alternatively, the substrate may comprise a composition deposited onto a web or other surface via an aqueous composition and subsequently dried to localize it on the web.

The laminate cleaning implement can have a rate of consumption. This is a measure of how much of the substrate is used during a usage event. If the consumption rate is too low, then cleaning can be difficult due to reduced access to the substrate and the active agents. However, if the consumption rate is too high, then the substrate and active agents can be released too quickly and the laminate cleaning composition can run out of substrate and/or active agent before the entire surface is cleaned. The consumption rate can vary based on the properties of the substrate and the sheets.

In one example, the laminate will have a consumption rate of about 3 g/use to about 30 g/use, in another example from about 6 g/use to about 25 g/use, and in another example from about 10 g/use to about 20 g/use as determined by the Consumption Rate Test described herein. In alternate examples, the laminate cleaning implement will have a consumption rate of about 0.5 g/use to about 15 g/use, in another example from about 1.5 g/use to about 10 g/use, and in another example from about 3.5 g/use to about 6.5 g/use as determined by the Consumption Rate Test described herein.

In one example, the laminate cleaning implement can further comprise an attachment means to attach or releasably attach the laminate cleaning implement to another article. Non-limiting examples of attachment means can include hook and loop fasteners such as Velcro®, buttons, fasteners, snaps, magnets, clips, adhesives, refastenable adhesives, and combinations thereof. The article can be a cleaning implement such as a broom, vacuum, sweeper, sponge, or toilet bowl cleaner. In one example, the attachment means is attached to or releasably attached to the backing sheet.

In another example, the laminate cleaning implement can be made into, affixed to, or releasably attached to, a glove, mitt, or other on-the-hand implement. In one example, the on-the-hand implement can be adapted so it is ambidextrous. In one example, the on-the hand implement comprises a water impermeable substrate or water impermeable sheet that is adapted to be in contact with the user's hand during use. The on-the-hand implement comprises a slip resistant substrate or slip resistant sheet, thereby preventing the on-the-hand implement from twisting or slipping during use. In one example the water impermeable substrate or water impermeable sheet is slip resistant.

In another example, the on-the-hand implement only covers the palm of the user's hand, and does not cover the user's fingers or back of the user's hand. This cleaning implement can be attached to the user's hand by any suitable attachment means including but not limited to Velcro®, an elastic strap, a buckle, or a tie.

In another example, the on-the-hand implement can be a mitt or glove and can comprise a grasping means. The grasping means can be a loop, hook, or tab. The grasping means can be attached to any portion of the on-the-hand implement. In one example, the grasping means can be attached to an interior portion of the on-the-hand implement and in another example the grasping means can be attached to an exterior portion and in another example the grasping means is attached to an exterior portion near a user's wrist. In another example, the grasping means can be formed by bonding the facing sheet to the backing sheet to provide a full or partial pocket, loop or hook, for one or more fingers of the user. The grasping means can also be attached to the water impermeable sheet or substrate. The grasping means can help a user turn the cleaning implement inside out as she takes it off her hand.

In another example, the on-the-hand implement comprises an adjustment means which can be any suitable means for permitting the on-the-hand implement to snugly accommodate different hand sizes. Suitable adjustment means, include but are not limited to, include, hook and loop fasteners such as Velcro® and the like, elastic members, elastic strands, strings including draw strings, gussets, cinches, buttons, fasteners, tabs, tongue and grove fasteners such as Zip-Lock® type fasteners, resealable tape, belts, clips, adhesives, such as refastenable adhesives, and combinations thereof.

In another example, the laminate cleaning implement can comprise a usage indicator. In one example, the usage indicator lets the user know when the laminate cleaning implement runs out of the substrate. The usage indicator can be a separate feature or it can be part of the substrate, or it may be a part of a graphic. Other suitable usage indicators can include, but are not limited to, pH (e.g., at a specific pH or pH range a noticeable event occurs such as color change, noise generation or cessation and the like and combinations thereof), temperature (e.g., the implement may feel warm or cold for its intended use and then revert to ambient temperature, or change temperature form ambient after a period of time), time (e.g., the indicator may change size shape, color etc. after a time period since it was exposed to water air, oxygen, shear or other force and the like), and the like and combinations thereof. In one example, the usage indicator can be a color that is associated with the substrate and the color changes or dissipates as the cleaning implement is used.

The facing sheet and/or backing sheet can comprise indicia. The indicia can be in the form of logos, trademarks, geometric patterns, images of the surfaces that the implement is intended to clean, instructions on how to use the cleaning implement including the function or purpose of one or both sides of the implement, other indicia, or combinations thereof.

The cleaning implement can be disposable. In one example, the cleaning implement is intended to be used only once before it is disposed of and contains enough substrate and active agent for one use. In another example, the cleaning implement can be adapted for multiple uses.

The cleaning implement can be packaged in a secondary container. In one example, the cleaning implement does not have to be individually wrapped and multiple cleaning implements can be packaged together in one secondary package. The secondary package can be any suitable package. Non-limiting examples can include a box, bag, and plastic and/or cellophane packaging.

In another example, the cleaning implement does not comprise a substrate. In another example, a liquid cleaning solution can be sprayed or poured onto the cleaning implement. This can be useful for spot-cleaning and/or in-between cleaning and can be sold in combination with a laminate cleaning implement comprising a substrate as a cleaning system. In one example, the two cleaning implements are co-packaged and in another example the two products are placed adjacent to or near each other in the store. In one example, a cleaning implement comprising a substrate can be used to bathe a pet and can be used in combination with an in-between cleaning implement that is an on-the-hand implement that does not comprise a substrate. The in-between implement can be sprayed with a liquid cleaning composition prior to use. The in-between implement can be used to spot clean areas like a pet's muzzle or paws or can be used to quickly refresh the entire pet. The in-between mitt can be used on a pet as needed, while the cleaning implement is intended to be used intermittently, for example once every two weeks.

The following examples are intended for illustrative purposes only and are not intended to limit the invention. Furthermore, the examples can be combined and duplicated to make more complex laminate cleaning implements, in particular cleaning implements with more than one substrate.

FIGS. 1-2 show a schematic representation of a portion of a bonded laminate web 60 suitable for use in a laminate cleaning implement of the present invention, hereinafter referred to simply as web 60. Web 60 can comprise three layers, backing sheet 61, facing sheet 62, and substrate 63. The layers should be sufficiently thin to be processible as described herein, but no actual thickness (i.e., caliper) is considered limiting.

As shown in FIG. 2, substrate 63 can be chosen such that when sheets 61 and 62 are processed, portions of substrate 63 can be "squeezed" or otherwise substantially displaced out of the plurality of bonding points 68 to permit the facing sheet 62 to bond directly to backing sheet 61 at bonding points 68. Thus, apertures in substrate 63 can be formed during bonding by displacement. In one example, substantially all of substrate 63 can be displaceable by the forces exerted by the processing equipment. In another example, the substrate can be apertured before the bonding process.

In an alternate example, the substrate can be involved, or participate, in the bonding between the facing and backing sheets. As used herein, "involved" refers to the substrate, to some extent, being in intimate contact with, and possibly partially merged with, one or both precursor webs. The involvement may be due to actual melt bonding within the bonding points and/or about the perimeter of bonding point or it may be due to mechanical interaction, such as by entanglement, also within the bonding points and/or about the perimeter of the bond point.

Sheets 61 and 62 can be thermally bondable and/or thermally compatible, and in one example backing sheet 61 and/or facing sheet 62 can be a nonwoven web comprising a sufficient quantity of thermoplastic material. For instance, if the precursor webs are thermally compatible they can have similar melting points. As used herein, "sufficient quantity" refers to a quantity of thermoplastic material adequate to enable enough thermal bonding upon application of heat and/or pressure to produce a unitary web. Backing sheet 61 and facing sheet 62 can be the same material or they can be different materials or structures.

Substrate 63 can be predisposed between backing sheet 61 and facing sheet 62. In one example, joining means provide a plurality of discrete bonding points 68 that serve to couple the sheets 61 and 62, and, in some examples, portions of substrate 63, thereby forming the constituent layers into a web. When joined together, sheets 61 and 62 form interior region 69 between them. Interior region 69 is the space between backing sheet 62 and facing sheet 61 that is surrounded by bonding points. In one example, the substrate can reside in and substantially fill the interior region. In another example, the substrate can reside in and at least partly or substantially fill the interior region. In one example, the substrate can fracture into pieces and the interior region in combination with the bonding pattern can stabilize the substrate. In another example, the substrate can be a powder or a multitude of small pieces that reside in and are stabilized by the interior region.

A plurality of discrete bonding points 68 can form bonding pattern 66. Bonding points 68 can be any shape. Non-limiting examples of shapes of bonding points can include rectangles, squares, circles, ovals, and combinations thereof. The bonding pattern 66 can be any design. Non-limiting examples of bonding patterns can include linear bonding patterns, cross-hatching bonding patterns, circular bonding patterns, square bonding patterns, regular repeating bonding patters, asymmetrical bonding patterns, and combinations thereof.

Bonding patterning 66 further includes sized spacing 67 between adjacent bonding points 68. As used herein, "adjacent bonding points" refers to two bonding points, which can be connected by a straight line that does not intersect or otherwise touch another bonding point. Such a sized spacing can provide a bonding pattern 66 in which the backing and facing sheets 61 and 62 are sufficiently adhered together such that neither the backing nor facing sheets exhibit significant tearing during use of the cleaning implement. In another example, the bonding pattern only covers a portion of the web or cleaning implement.

In one example, the sized spacing 67 is from about 0.5 mm to about 25 mm, in another example from about 1 mm to about 20 mm, and in another example from about 2 mm to about 10 mm. In one example the greatest sized spacing is less than about 25 mm, in another example less than about 23 mm, in another example less than about 20 mm, in another example less than about 15 mm, in another example less than about 10 mm, and in another example less than about 5 mm.

Additional information on bonded laminate webs can be found in U.S. Pat. No. 7,037,569.

FIG. 3 shows a schematic representation of a cross-sectional view of a laminate cleaning implement 100, hereinafter simply referred to as laminate 100. Laminate 100 comprises textured web 104, bonded laminate web 106, and water impermeable layer 105. Textured web 104, bonded laminate web 106, and water impermeable layer 105 can be joined at the edges and/or intermediate locations by any joining means.

Non-limiting examples of joining means can include mechanical or geometric interpenetration, interlocking, sewing, adhesive, and combinations thereof. Textured web 104 can be water permeable. Textured laminate web can include any texture. Non-limiting examples of textures can include protrusions, depressions, apertures, embossing, debossing, and combinations thereof. The textured portion can improve the cleaning functionality of the laminate cleaning implement. In one example, the textured portions can be made by SELFing, which creates protrusions that extend outwardly from the facial sheet, referred to herein as tufts, on one side of the laminate cleaning implement and depressions, referred to herein as indentations, on the opposite side of the laminate cleaning implement.

The bonded laminate web 106 is made similarly to the bonded laminate web in FIGS. 1-2. The bonded laminate web can comprise three layers, a backing sheet 101, facing sheet 102, and substrate 103, which is disposed between the backing sheet 101 and the facing sheet 102.

Textured web 104 can provide additional friction to help with cleaning, penetration of wet hair or fur, or capacity to hold later and/or remove debris or other contaminants. Textured web 104 can cover the entire surface or portions of bonded laminate web 106.

Component Materials for Facing Sheet and Backing Sheet

The laminate cleaning implement can comprise one or more sheets. The sheets can comprise any suitable material. Suitable materials can be resilient enough that they resist tearing or shredding during normal use. In another example, the sheet(s) can be incorporated into a cleaning implement that can be used to wash a human or pet and therefore the sheets can be made out of a material that limits irritation to a user's skin. In another example, the laminate cleaning implement can also be subjected to a mechanical deformation process, such as SELFing, and thus a suitable material can be capable of experiencing sufficient tensile elongation and plastic deformation, or are capable of sufficient fiber mobility, such that out-of-plane texture is formed.

The sheets can comprise any suitable material including polymer films, woven webs, or nonwoven webs. In one example, the facing sheet and/or the backing sheet can be a nonwoven web comprised of substantially randomly oriented fibers. By "substantially randomly oriented" is meant that, due to processing conditions of the sheet, there may be a higher amount of fibers oriented in the MD than the CD, or vice-versa.

Nonwovens can be made out of a plurality of fibers which can include, natural fibers, synthetic fibers, and combinations thereof. In another example, the nonwovens can comprise a high loft batting material. High loft batting material has a low density, as compared to similar non-high loft nonwoven material, and comprises a random array of void spaces throughout its structure. High loft batting material can help the substrate lather. In another example, the nonwovens can be an airlaid nonwoven material comprising a combination of natural fibers, staple length synthetic fibers and a latex binder. The nonwoven material can be about 20% to about 80% by weight wood pulp fibers, about 10% to about 60% by weight staple length polyester fibers, and about 10% to about 25% by weight binder. In one example, the high loft batting material is incorporated into a sheet that is adapted to be adjacent to the user's hand when the implement is in use. In another example the high loft batting material is incorporated into a layer that is adjacent to the substrate.

In another example, the sheets can comprise an elastomer. The elastomer can be elastic strands and/or an elastic film. Any suitable elastic film known in the art can be used. Suitable elastic films may comprise polypropylene, polyethylene, polyolefins, styrene-isoprene-styrene, styrene-butadiene-styrene, or combinations thereof. Suitable elastic strands can be made of a resilient elastic thermoplastic material. Additional information on elastomers can be found in U.S. Pat. No. 7,432,413 and U.S. patent application Ser. No. 12/687,527; abandoned Oct. 6, 2015.

In another example, the sheets can be biodegradable. For example, the implement or components thereof could be made from a biodegradable material, such as a polyesteramide.

Suitable natural fibers for constructing the nonwoven webs can include but are not limited to cellulosic fibers, such as wood pulp fibers, cotton, and rayon. Suitable synthetic fibers include fibers commonly used in textiles, including but not limited to polyester (e.g. polyethylene terephthalate) and polypropylene, polyethylene, polyether, and combinations thereof. Suitable fibers can be made of biopolymers made from non-petroleum sources such as bio-derived polyethylene (bio-PE), bio-derived polypropylene (bio-PP), bio-derived polyethylene terephthalate (bio-PET), and bio-derived poly(ethylene-2,5-furandicarboxylate) (bio-PEF). These materials can be partially or completely derived from at least one renewable resource where a renewable resource refers to a natural resource that can be replenished within a 100 year time frame. Renewable resources include plants, animals, fish, bacteria, fungi, and forestry products and may be naturally occurring, hybrids, or genetically engineered organisms. Natural resources such as crude oil, coal, and peat which take longer than 100 years to form are not considered to be renewable resources. Other polymers derived from non-petroleum sources include starch-based polymers and cellulosics. Additionally, recycled resins such as post-consumer regrind r-HDPE, r-LLDPE, r-LDPE, r-PET, r-PEF, or r-PP can be used at 100% or blended with various resins. Polymers derived from renewable resources and recycled resins could be used on their own, or blended into petroleum-based polymers at varying levels in order to control the cost. Sources and methods of making polymers from non-petroleum sources can be found in U.S. App. No. 2011/0319849.

Various methods can be used to form the facing sheet and the backing sheet for use in the present invention. For instance, if the sheets are nonwoven webs they can be made by nonwoven dry forming techniques, such as air-laying, or alternatively by wet laying, such as on a papermaking machine, of a continuous web out of which the nonwoven webs are made. Other nonwoven manufacturing techniques, including but not limited to techniques such as spunbonding, meltblowing, carding, needle punching, hydroentangling, thermal bonding, through-air bonding, lamination methods may also be used, and combinations thereof.

The sheets can be subjected to various treatments, such as, but not limited to, physical treatment, such as aperturing, embossing, ring rolling SELFing and the like; chemical treatment, such as, rendering part or all of the sheet hydrophobic, and/or hydrophilic, and the like; thermal treatment, such as softening of fibers by heating, thermal bonding and the like; and combinations thereof.

Additional information on materials which are suitable for use as the sheets of the present invention can be found in the following patents: U.S. Pat. Nos. 3,862,472; 3,982,302; 4,004,323; 4,057,669; 4,097,965; 4,176,427; 4,130,915; 4,135,024; 4,207,367; 4,296,161; 4,682,942; 4,637,859; 5,223,096; 5,240,562; 5,556,509; and 5,580,423.

Substrates

After exposure to conditions of intended use, the substrate comprising an active can release the active agent and it can be spread across the area to be treated using the cleaning implement. The substrate can be lathering or non-lathering after exposure to conditions of intended use.

The substrate can releasably comprise an active agent. The active agent can be on the substrate or in the substrate and can be released when it the cleaning implement comes into contact with conditions of intended use, such as water.

Non-limiting examples of substrates can include open cell foams, dissolvable filament substrates, compliant doughs, films, fibers including nonwoven fibers, webs, powders, closed cell foams, pastes, substantially dry solids, particles, flakes, and combinations thereof. In another example, the substrate can be a semi-solid or liquid substrate.

The substrate can be disposed between the facing sheet and the backing sheet. The substrate can be disposed on substantially the entire cleaning implement or a portion of the cleaning implement. In one example, the substrate can be a flat, flexible substrate in the form of a pad, a strip, sheet or tape. In another example, the substrate is not completely plastically deformable and it may be broken, cracked, or fractured and held into place via the structure of the laminate cleaning implement. In yet another example, the substrate can be a particulate composition, which can be made of small particles, similar to sand, and/or larger particles, similar to pellets, or anything in-between.

The substrate may comprise a coating deposited onto a web via an aqueous solution an subsequently dried (i.e., water removed) to form at least a partial film on elements of the web.

The substrate can be mostly dry, even dry to the touch, prior to being exposed to conditions of intended use. In one example, the substrate comprises less than or equal to about 10% moisture, such as water, by weight of substrate, in another example less than or equal to about 7%, in another example less than or equal to about 5%, and in another example less than or equal to about 3%, as determined by the Water Content Test Method described herein.

The substrate can quickly dissolve after it is exposed to conditions of intended use. In one example, the substrate can dissolve in less than about 60 seconds/gram (s/g), in another example less than about 30 s/g, in another example less than 20 s/g, in another example less than about 15 s/g, in another example less than about 10 s/g, in another example less than about 7 s/g, as determined by the Dissolution Test Method described herein.

The substrate can comprise an active agent which can be a surfactant, a polymer, and/or a plasticizer. When the cleaning implement is intended to be used on the skin, mucous membranes, scalp, or hair of a human or pet, all components of the substrate can be physiologically acceptable, i.e., they can be compatible with the skin, mucous membranes, the hair and/or the scalp.

The substrate can comprise a surfactant. In one example, the substrate is a lathering substrate and the surfactant can be a foaming agent.

Non-limiting examples of suitable surfactants can include anionic surfactants, cationic surfactants, nonionic surfactants, zwitterionic surfactants, amphoteric surfactants, and combinations thereof. For a substrate designed for use as soap, detergent, or shampoo the total level of surfactants should be sufficient to provide cleaning including stain, oil, dirt, and/or odor removal, and generally ranges from about 0.5% to about 95%. Further, surfactant systems comprising two or more surfactants that are designed for use in substrates may include all-anionic surfactant systems, mixed-type surfactant systems comprising anionic-nonionic surfactant mixtures, or nonionic-cationic surfactant mixtures or low-foaming nonionic surfactants.

Non limiting examples of anionic surfactants are described in U.S. Pat. Nos. 2,486,921, 2,486,922, and 2,396,278. Non limiting examples of anionic surfactants can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic surfactants are described in U.S. Pat. Nos. 5,104,646 and 5,106,609.

Non-limiting examples of suitable cationic surfactants are described in U.S. Pat. Nos. 4,228,042, 4,239,660, 4,260,529, 6,022,844, 6,004,922, 6,136,769, and 6,221,825.

Non-limiting examples of suitable nonionic surfactants include alkoxylated alcohols (AE's) and alkyl phenols, polyhydroxy fatty acid amides (PFAA's), alkyl polyglycosides (APG's), $C_{10}$-$C_{18}$ glycerol ethers, and the like. Additional suitable nonionic surfactants can be found in U.S. Pat. Nos. 4,133,779, 4,483,779, 4,681,704, 4,483,780, 4,565,647, and 6,482,994.

Additional suitable surfactants include those disclosed in U.S. Pat. No. 8,309,505 and those surfactants disclosed in McCutcheon's Detergents and Emulsifiers, North American Edition (1986), Allured Publishing Corp.; McCutcheon's, Functional Materials, North American Edition (1992), Allured Publishing Corp.

In another example, the substrate can comprise a polymer. Non-limiting examples of polymers can include synthetic polymers as described in U.S. Pat. No. 8,349,787 including polymers derived from acrylic monomers such as the ethylenically unsaturated carboxylic monomers and ethylenically unsaturated monomers as described in U.S. Pat. No. 5,582,786. The polymers which are suitable may also be selected from naturally sourced polymers including those of plant origin examples which are described in U.S. App. No. 61/120,786. Modified natural polymers are also useful as water-soluble polymer(s) in the present invention and are included in U.S. Pat. No. 8,349,787.

In one example, polymers can include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methycelluloses, carboxymethycelluloses, and combinations thereof. Suitable polyvinyl alcohols can include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

In another example, the polymer can comprise a polysaccharide, such as starch and/or a starch derivative, such as an ethoxylated starch and/or acid-thinned starch. Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof.

In another example, the substrate can comprise a plasticizer. Non-limiting examples of plasticizers can include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid.

In one example, the plasticizer can include glycerin and/or propylene glycol and/or glycerol derivatives such as propoxylated glycerol. In still another example, the plasticizer can be selected from the group consisting of glycerin, ethylene glycol, polyethylene glycol, propylene glycol, glycidol, urea, sorbitol, xylitol, maltitol, sugars, ethylene bisformamide, amino acids, and mixtures thereof In another example, the substrate can comprise one or more colors and/or dyes that are incorporated into the substrate or are on the substrate. In one example, the colors and/or dyes can provide a visual signal when the substrate has been exposed to conditions of intended use and/or when an active agent is released from the substrate.

In one example, the substrate can be an open cell foam. The open cell foam can have a high degree of cell inter-connectivity. While not wishing to be bound by theory, it is believed that due to the high degree of cell inter-connectivity, the open cell foam can dissolve faster than a closed cell foam. The open cell foam can have a minimum level of interconnectivity between the cells, which is quantified by the Percent Open Cell Content.

The open cell foam can have a Percent Open Cell Content of from about 80% to about 100%, in one example from about 85% to about 97.5%, and in another example from about 90% to about 95%. The Percent Open Cell Content can be determined using the Gas Pycnometry Method described herein.

The open cell foam can have a minimum specific surface area. The open cell foam can have a specific surface area of from about 0.03 $m^2/g$ to about 0.25 $m^2/g$, in one example from about 0.035 $m^2/g$ to about 0.22 $m^2/g$, in another example from about 0.04 $m^2/g$ to about 0.19 $m^2/g$, and in still another example from about 0.045 $m^2/g$ to about 0.16 $m^2/g$. The specific surface area can be determined using the Specific Surface Area Method described herein.

In one example, the open cell foam can be a lathering foam and can comprise a surfactant and the surfactant can be present from about 10% to about 75%, in another example from about 30% to about 70%, and in another example from about 40% to about 65% by weight of the substrate. In another example, the open cell foam dissolvable solid substrate is a non-lathering open cell foam and can comprise from about 10% to about 75%, in another example from about 15% to about 60%, and in another example from about 20% to about 50% by weight of the foam; wherein the surfactant comprises one or more of the surfactants described herein.

In one example, the open cell foam can comprise a polymer and the polymer may be present from about 10% to about 50% by weight of the foam, in one example from about 15% to about 40% by weight of the foam, and in yet another example from about 20% to about 30% by weight of the foam.

The open cell foam can comprise a plasticizer. In one example, the plasticizers can be present from about 1% to about 30% by weight of the foam; in another example from about 3% to about 25%; in another example from about 5% to about 20%, and in yet another example, from about 8% to about 15%.

Open celled foams as described herein can be made using the following method: (1) Preparing a processing mixture comprising surfactant(s), a polymer, and plasticizer; (2) Aerating the processing mixture by introducing a gas into the processing mixture to form an aerated wet mixture; (3) Forming the aerated wet mixture into one or more desired shapes; and (4) Drying the aerated wet mixture to form a porous dissolvable solid substrate.

The processing mixture is generally prepared by dissolving a polymer in the presence of water, a plasticizer, and a surfactant by heating followed by cooling. Then, the processing mixture is aerated, which can be accomplished by any means that introduces a gas into the mixture to form the aerated wet processing mixture. In one example, a continuous pressurized aerator (available from Morton Machine Co., Motherwell, Scotland) that is conventionally utilized within the foods industry can be used.

Then, the wet aerated processing mixture can be formed into the desired shape or shapes. One way to do this is to deposit the wet aerated mixture into one or more molds. Finally, the wet aerated processing mixture is dried. One way to dry the wet aerated mixture is to place it in a heated drying room with a temperature between 100° C. and 150° C. After the mixture is dried, an open cell foam is created and can be removed from the molds if necessary.

Additional information on making open cell foams is disclosed in U.S. patent application Ser. No. 13/561,298; now U.S. Pat. No. 8,476,211.

In one example, the substrate can be a dissolvable filament substrate. The dissolvable filament substrate can comprise filaments and/or fibers that can be interlaid and can be randomly oriented. In one example, the dissolvable filament substrate comprises filaments.

As used herein, "filament" means an elongate particulate having a length greatly exceeding its diameter, i.e. a length to diameter ratio of at least about 10.

The filaments of can be spun from filament-forming compositions via suitable spinning processes operations, such as meltblowing and/or spunbonding.

The filaments can be monocomponent, bicomponent and/or multicomponent.

Filaments are typically considered continuous or substantially continuous in nature. Filaments are relatively longer than fibers (which are less than 5.08 cm in length).

In one example, one or more fibers may be formed from a filament as described herein, such as when the filaments are cut to shorter lengths (such as less than 5.08 cm in length). Thus, in one example, the fiber made from a filament as described herein, such as a fiber comprising one or more filament-forming materials. Therefore, references to filament and/or filaments also include fibers made from such filament and/or filaments unless otherwise noted. Fibers are typically considered discontinuous in nature relative to filaments, which are considered continuous in nature.

As used herein, "filament-forming material" means a material, such as a polymer or monomers capable of producing a polymer that can exhibit properties suitable for making a filament.

The filament-forming material can be any suitable material, such as a polymer or monomers capable of producing a polymer that exhibits properties suitable for making a filament, such as by a spinning process.

In one example, the filament comprises about 100% and/or greater than about 95% and/or greater than about 90% and/or greater than about 85% and/or greater than about 75% and/or greater than about 50% by weight on a dry filament basis and/or dry dissolvable filament substrate basis of one or more filament-forming materials. For example, the filament-forming material can comprise a polymer and in one example the polymer is a polyvinyl alcohol and/or starch.

As used herein, "by weight on a dry filament basis and/or dry dissolvable filament substrate basis" means that the weight of the filament and/or dissolvable filament substrate measured immediately after the filament and/or dissolvable filament substrate has been conditioned in a conditioned room at a temperature of 73° F.±4° F. (about 23° C.±2.2° C.) and a relative humidity of 50%±10% for 2 hours. In one example, "by weight on a dry filament basis and/or dry dissolvable filament substrate basis" means that the filament and/or dissolvable filament substrate comprises less than 20% and/or less than 15% and/or less than 10% and/or less than 7% and/or less than 5% and/or less than 3% and/or to 0% and/or to greater than 0% based on the weight of the filament and/or dissolvable filament substrate of moisture, such as water, for example free water, as measured according to the Water Content Test Method described herein.

In another example, the filament comprises one or more filament-forming materials and one or more active agents wherein the total level of filament-forming materials present in the filament is from about 5% to less than about 80% by weight on a dry filament basis and/or dry dissolvable filament substrate basis and the total level of active agents present in the filament is greater than about 20% to about 95% by weight on a dry filament basis and/or dry dissolvable filament substrate basis.

In another example, the filament-forming materials and active agents are present in the filament at a weight ratio of total level of filament-forming materials to active agents of about 4.0 or less and/or about 3.5 or less and/or about 3.0 or less and/or about 2.5 or less and/or about 2.0 or less and/or about 1.85 or less and/or less than about 1.7 and/or less than about 1.6 and/or less than about 1.5 and/or less than about 1.3 and/or less than about 1.2 and/or less than about 1 and/or less than about 0.7 and/or less than about 0.5 and/or less than about 0.4 and/or less than about 0.3 and/or greater than about 0.1 and/or greater than about 0.15 and/or greater than about 0.2.

In still another example, the filament comprises from about 10% and/or from about 15% to less than about 80% by weight on a dry filament basis and/or dry dissolvable filament substrate basis of a filament-forming material, such as polyvinyl alcohol polymer and/or a starch polymer, and greater than about 20% to about 90% and/or to about 85% by weight on a dry filament basis and/or dry dissolvable filament substrate basis of an active agent.

As used herein, "filament-forming composition" means a composition that is suitable for making a filament such as by meltblowing and/or spunbonding. The filament-forming composition comprises one or more filament-forming materials that exhibit properties that make them suitable for spinning into a filament. In one example, the filament-forming composition can comprise a polymer. In one example, the filament-forming composition may comprise one or more active agents. In another example, the filament-forming composition can comprise a polar solvent, such as water, into which some or all, of the filament-forming materials and/or the active agents are dissolved and/or dispersed. In another example, the filament-forming composition can comprise a plasticizer.

In another example, the filament and/or the filament-forming composition can comprise a crosslinking agent suitable for crosslinking one or more of the filament-forming materials present in the filaments of the present invention. In one example, the crosslinking agent comprises a crosslinking agent capable of crosslinking hydroxyl polymers together, for example via the hydroxyl polymers hydroxyl moieties. Non-limiting examples of suitable crosslinking agents include imidazolidinones, polycarboxylic acids and mixtures thereof. In one example, the crosslinking agent comprises a urea glyoxal adduct crosslinking agent, for example a dihydroxyimidazolidinone, such as dihydroxyethylene urea ("DHEU").

In one example the filament does not contain cellulose. As used herein, "non-cellulose-containing" means that less than about 5% and/or less than about 3% and/or less than about 1% and/or less than about 0.1% and/or about 0% by weight of cellulose polymer, cellulose derivative polymer and/or cellulose polymer is present in filament.

The dissolvable filament substrates can be made by any suitable method, including the methods in U.S. Pat. No. 7,291,300 and U.S. patent application Ser. No. 13/229,818; Publication No. 2012/0027838 A1 now pending.

In addition, a plurality of the filaments can be collected and pressed into a film, thus resulting in a dissolvable film substrate comprising the one or more filament-forming materials and the one or more active agents that are releasable from the dissolvable film, such as when the film is exposed to conditions of intended use.

Laminate Cleaning Implement

One or more of the facing sheet, backing sheet, and the substrate may further comprise a soil capture agent that facilitates removal of soils from the surfaces being cleaned. "Soil" refers to organic or inorganic material, often particulate in nature that may include dirt, clays, food particulates, sebum or greasy residue, soot, etc. The soil capture agent may remain with the laminate cleaning implement such that soil removed from a surface becomes captured in and/or bound and/or adhered to and/or entrapped in the laminate cleaning implement.

A soil capture agent as described herein provides enhanced benefits in capturing soil. Such soil capture agents can be used singularly or in combination with other components to form a cleaning composition (e.g., liquid cleansing solution). In certain embodiments, such soil capture agents can include polymers. Such polymers can include several monomeric units thus it can be referred to as a copolymer rather than a homopolymer, which consists of a single type of monomeric unit. The polymers of the present disclosure may be a terpolymer (3 different monomeric units). The polymers of the present disclosure may be a random copolymer. In one example, a polymer of the present disclosure may be water-soluble and/or water-dispersible, which means that the polymer does not, over at least a certain pH and concentration range, form a two-phase composition in water at 23° C.±2.2° C. and a relative humidity of 50%±10%.

In one example, the polymers of the present invention exhibit a Number Average Molecular Weight of less than 2,000,000 g/mol and/or less than 1,750,000 g/mol and/or less than 1,700,000 g/mol and/or less than 1,500,000 g/mol and/or greater than 500,000 g/mol and/or greater than 900,000 g/mol. In another example, the polymers exhibit a Number Average Molecular Weight of from about 500,000 to 2,000,000 g/mol and/or from about 900,000 to 1,700,000 g/mol and/or from about 1,000,000 to 1,500,000 g/mol.

In yet another example, the polymers of the present invention exhibit a charge density (at pH 4.5) of from about −0.1 meq/g and/or from about −0.05 meq/g and/or from about −0.02 meq/g and/or from about 0 meq/g and/or to about +0.1 meq/g and/or to about +0.09 meq/g and/or to about +0.08 meq/g and/or to about +0.06 meq/g and/or to about +0.05 meq/g and/or to about +0.02 meq/g as measured according to the Charge Density Test Method described herein. In still another example, the polymers of the present invention exhibit a charge density of from about −0.1 meq/g to about +0.1 meq/g and/or from −0.05 meq/g to about +0.1 meq/g and/or from about 0 to less than +0.1 meq/g and/or to less than +0.09 meq/g and/or to less than +0.08 meq/g and/or to less than +0.06 meq/g and/or to less than +0.05 meq/g as measured according to the Charge Density Test Method described herein. In one example, the polymers of the present invention exhibit an excess charge (charge density) of from about 0 to about 0.1 meq/g. In another example, the polymers of the present invention exhibit an excess charge (charge density) of about 0.05 meq/g or less.

In another example, the polymers exhibit a Polydispersity Index of less than 2.5 and/or of less than 2.0 and/or less than 1.7 and/or less than 1.5 and/or less than 1.3.

In one example, a polymer of the present invention comprises two or more monomeric units selected from the group consisting of: a. nonionic monomeric units; b. anionic monomeric units; c. cationic monomeric units; d. zwitterionic monomeric units; and e. mixtures thereof.

a. Nonionic Monomeric Units

The nonionic monomeric units may be selected from the group consisting of: nonionic hydrophilic monomeric units, nonionic hydrophobic monomeric units, and mixtures thereof.

Non-limiting examples of nonionic hydrophilic monomeric units suitable for the present invention include nonionic hydrophilic monomeric units derived from nonionic hydrophilic monomers selected from the group consisting of: hydroxyalkyl esters of $\alpha,\beta$-ethylenically unsaturated acids, such as hydroxyethyl or hydroxypropyl acrylates and methacrylates, glyceryl monomethacrylate, $\alpha,\beta$-ethylenically unsaturated amides such as acrylamide, N,N-dimethylmethacrylamide, N-methylolacrylamide, $\alpha,\beta$-ethylenically unsaturated monomers bearing a water-soluble polyoxyalkylene segment of the poly(ethylene oxide) type, such as poly(ethylene oxide) $\alpha$-methacrylates (Bisomer S20W, S10W, etc., from Laporte) or $\alpha,\omega$-dimethacrylates, Sipomer BEM from Rhodia ($\omega$-behenyl polyoxyethylene methacrylate), Sipomer SEM-25 from Rhodia ($\omega$-tristyrylphenyl polyoxyethylene methacrylate), $\alpha,\beta$-ethylenically unsaturated monomers which are precursors of hydrophilic units or segments, such as vinyl acetate, which, once polymerized, can be hydrolyzed in order to give rise to vinyl alcohol units or polyvinyl alcohol segments, vinylpyrrolidones, $\alpha,\beta$-ethylenically unsaturated monomers of the ureido type, and in particular 2-imidazolidinone-ethyl methacrylamide (Sipomer WAM II from Rhodia), and mixtures thereof. In one example, the nonionic hydrophilic monomeric unit is derived from acrylamide.

Non-limiting examples of nonionic hydrophobic monomeric units suitable for the present invention include nonionic hydrophobic monomeric units derived from nonionic hydrophobic monomers selected from the group consisting of: vinylaromatic monomers such as styrene, alpha-methylstyrene, vinyltoluene, vinyl halides or vinylidene halides, such as vinyl chloride, vinylidene chloride, $C_1$-$C_{12}$ alkylesters of $\alpha,\beta$-monoethylenically unsaturated acids such as methyl, ethyl or butyl acrylates and methacrylates, 2-ethylhexyl acrylate, vinyl esters or allyl esters of saturated carboxylic acids, such as vinyl or allyl acetates, propionates, versatates, stearates, $\alpha,\beta$-monoethylenically unsaturated nitriles containing from 3 to 12 carbon atoms, such as acrylonitrile, methacrylonitrile, $\alpha$-olefins such as ethylene, conjugated dienes, such as butadiene, isoprene, chloroprene, and mixtures thereof.

b. Anionic Monomeric Units

Non-limiting examples of anionic monomeric units suitable for the present invention include anionic monomeric units derived from anionic monomers selected from the group consisting of: monomers having at least one carboxylic function, for instance $\alpha,\beta$-ethylenically unsaturated carboxylic acids or the corresponding anhydrides, such as acrylic, methacrylic or maleic acids or anhydrides, fumaric acid, itaconic acid, N-methacroylalanine, N-acryloylglycine, and their water-soluble salts, monomers that are precursors of carboxylate functions, such as tert-butyl acrylate, which, after polymerization, give rise to carboxylic functions by hydrolysis, monomers having at least one sulfate or sulfonate function, such as 2-sulfooxyethyl methacrylate, vinylbenzene sulfonic acid, allyl sulfonic acid, 2-acrylamido-2-methylpropane sulfonic acid (AMPS), sulfoethyl acrylate or methacrylate, sulfopropyl acrylate or methacrylate, and their water-soluble salts, monomers having at least one phosphonate or phosphate function, such as vinylphosphonic acid, etc., the esters of ethylenically unsaturated phosphates, such as the phosphates derived from hydroxyethyl methacrylate (Empicryl 6835 from Rhodia) and those derived from polyoxyalkylene methacrylates, and their water-soluble salts, and 2-carboxyethyl acrylate (CEA), and mixtures thereof. In one example, the anionic monomeric unit is derived from an anionic monomer selected from the group consisting of: acrylic acid, AMPS, CEA, and mixtures thereof. In another example, the anionic monomeric unit is derived from acrylic acid.

c. Cationic Monomeric Units

Non-limiting examples of cationic monomeric units suitable for the present invention include cationic monomeric units derived from cationic monomers selected from the group consisting of: N,N-(dialkylamino-$\omega$-alkyl)amides of $\alpha,\beta$-monoethylenically unsaturated carboxylic acids, such as N,N-dimethylaminomethylacrylamide or -methacrylamide, 2-(N,N-dimethylamino)ethylacrylamide or -methacrylamide, 3-(N,N-dimethylamino)propylacrylamide or -methacrylamide, and 4-(N,N-dimethylamino)butylacrylamide or -methacrylamide, $\alpha,\beta$-monoethylenically unsaturated amino esters such as 2-(dimethylamino)ethyl acrylate (DMAA), 2-(dimethylamino)ethyl methacrylate (DMAM), 3-(dimethylamino)propyl methacrylate, 2-(tert-butylamino)ethyl methacrylate, 2-(dipentylamino)ethyl methacrylate, and 2(diethylamino)ethyl methacrylate, vinylpyridines, vinylamine, vinylimidazolines, monomers that are precursors of amine functions such as N-vinylformamide, N-vinylacetamide, which give rise to primary amine functions by simple acid or base hydrolysis, acryloyl- or acryloyloxyammonium monomers such as trimethylammonium propyl methacrylate chloride, trimethylammonium ethylacrylamide or -methacrylamide chloride or bromide, trimethylammonium butylacrylamide or -methacrylamide methyl sulfate, trimethylammonium propylmethacrylamide methyl sulfate, (3-methacrylamidopropyl)trimethylammonium chloride (MAPTAC), (3-methacrylamidopropyl)trimethylammonium methyl sulphate (MAPTA-MES), (3-acrylamidopropyl)trimethylammonium chloride (APTAC), methacryloyloxyethyl-trimethylammonium chloride or methyl sulfate, and acryloyloxyethyltrimethylammonium chloride; 1-ethyl-2-vinylpyridinium or 1-ethyl-4-vinylpyridinium bromide, chloride or methyl sulfate; N,N-dialkyldiallylamine monomers such as N,N-dimethyldiallylammonium chloride (DADMAC); polyquaternary monomers such as dimethylaminopropylmethacrylamide chloride and N-(3-chloro-2-hydroxypropyl)trimethylammonium (DIQUAT or DQ) and 2-hydroxy-$N^1$-(3-(2((3-methacrylamidopropyl)dimethylamino)-acetamido)propyl)-$N^1,N^1,N^3,N^3,N^3$-pentamethylpropane-1,3-diaminium chloride (TRIQUAT or TQ), and mixtures thereof. In one example, the cationic monomeric unit comprises a quaternary ammonium monomeric unit, for example a monoquaternary ammonium monomeric unit, a diquaternary ammonium monomeric unit and a triquaternary monomeric unit. In one example, the cationic monomeric unit is derived from MAPTAC. In another example, the cationic monomeric unit is derived from DADMAC. In still another example, the cationic monomeric unit is derived from TQ.

In one example, the cationic monomeric units are derived from cationic monomers selected from the group consisting of: dimethylaminoethyl (meth)acrylate, dimethylaminopropyl (meth)acrylate, di-tert-butylaminoethyl (meth)acrylate, dimethylaminomethyl (meth)acrylamide, dimethylaminopropyl (meth)acrylamide, ethylenimine, vinylamine, 2-vinylpyridine, 4-vinylpyridine and vinyl imidazole, and mixtures thereof.

In another example, the cationic monomeric units are derived from cationic monomers selected from the group consisting of: trimethylammonium ethyl (meth)acrylate bromide, chloride or methyl sulfate, trimethylammonium ethyl (meth)acrylate bromide, chloride or methyl sulfate, trimethylammonium ethyl (meth)acrylate bromide, chloride or methyl sulfate, dimethylaminoethyl (meth)acrylate benzyl chloride, 4-benzoylbenzyl dimethylammoniumethyl (meth) acrylate bromide, chloride or methyl sulfate, trimethylammonium ethyl (meth)acrylamido bromide, chloride, or methyl sulfate, trimethylammonium propyl (meth)acrylamido braomide, chloride, or methyl sulfate, vinyl benzyl trimethyl ammonium bromide, chloride or methyl sulfate, diallyldimethyl ammonium chloride, 1-ethyl-2-vinylpyridinium bromide, chloride or methyl sulfate, 4-vinylpyridinium bromide, chloride or methyl sulfate, and mixtures thereof.

d. Zwitterionic Monomeric Units

Non-limiting examples of zwitterionic monomeric units suitable for the present invention include zwitterionic monomeric units derived from zwitterionic monomers selected from the group consisting of: sulfobetaine monomers, such as sulfopropyl dimethylammonium ethyl methacrylate (SPE from Raschig), sulfopropyldimethylammonium propylmethacrylamide (SPP from Raschig), and sulfopropyl-2-vinylpyridinium (SPV from Raschig), 3-((3-methacrylamidopropyl)dimethylammonio)propane-1-sulfonate (SZ), phosphobetaine monomers, such as phosphatoethyl trimethylammonium ethyl methacrylate, carboxybetaine monomers, N-(carboxymethyl)-3-methacrylamido-N,N-dimethlpropan-1-aminium chloride (CZ). In one example, the zwitterionic monomeric unit is derived from CZ, SZ, and mixtures thereof.

In one example, a polymer of the present invention may comprise at least one monomeric unit selected from groups a (nonionic monomeric units) and b (anionic monomeric units) and at least one monomeric unit selected from groups c (cationic monomeric units) and d (zwitterionic monomeric units).

In one example, the polymer comprises at least 69.9% wt and/or at least 70% wt and/or at least 75% wt and/or at least 80% wt and/or at least 85% wt and/or at least 90% wt and/or at least 95% wt and/or at least 98% wt and/or at least 99% wt and/or at least 99.5% wt of a monomeric unit from group a. The balance of the polymer (no more than 30.1% wt and/or no more than 30% wt and/or no more than 25% wt and/or no more than 20% wt and/or no more than 15% wt and/or no more than 10% wt and/or no more than 5% wt and/or no more than 2% wt and/or no more than 1% wt and/or no more than 0.5% wt total) comprises one or more monomeric units selected from groups b, c, and d. In one example, the polymer comprises from about 70% to about 99.5% wt of a monomeric unit from group a, from about 0.1% to about 10% wt of a monomeric unit from group b, and from about 0.3% to about 29% wt of a monomeric unit from group c. In still another example, the polymer comprises from about 70% to about 99.5% wt of a monomeric unit from group a, from about 0.5% to about 30% wt combined of monomeric units from groups b and c.

In one example, the polymer comprises at least 0.1% wt and/or at least 1% and/or at least 5% wt and/or at least 7% wt and/or at least 10% wt and/or to about 25% wt and/or to about 20% wt and/or to about 15% wt of a monomeric unit from group b.

In one example, polymer comprises at least 0.1% wt and/or at least 0.3% wt and/or at least 0.5% and/or at least 1% and/or at least 5% wt and/or at least 7% wt and/or at least 10% wt and/or to about 75% wt and/or to about 70% wt and/or to about 65% wt and/or to about 55% wt and/or to about 40% wt and/or to about 30% wt and/or to about 25% wt and/or to about 20% wt and/or to about 15% wt of a monomeric unit from group c.

In one example, polymer comprises at least 0.1% wt and/or at least 0.3% wt and/or at least 1% and/or at least 5% wt and/or at least 7% wt and/or at least 10% wt and/or to about 75% wt and/or to about 70% wt and/or to about 65% wt and/or to about 55% wt and/or to about 40% wt and/or to about 30% wt and/or to about 25% wt and/or to about 20% wt and/or to about 15% wt of a monomeric unit from group d.

In another example, the polymer comprises no more than 30.1% wt of a monomeric unit selected from the group consisting of: group b, group c, group d, and mixtures thereof.

In one example, the polymer may comprise a monomeric unit from group a and a monomeric unit from group b.

In one example, the polymer may comprise a monomeric unit from group a and a monomeric unit from group c.

In another example, the polymer of the present invention may comprise a monomeric unit from group a and a monomeric unit from group d.

In still another example, the polymer of the present invention may comprise a monomeric unit from group b and a monomeric unit from group c.

In still another example, the polymer of the present invention may comprise a monomeric unit from group b and a monomeric unit from group d.

In still another example, the polymer of the present invention may comprise a monomeric unit from group c and a monomeric unit from group d.

In yet another example, the polymer of the present invention may comprise a monomeric unit from group a, a monomeric unit from group b, and a monomeric unit from group c.

In even another example, the polymer of the present invention may comprise a monomeric unit from group a, a monomeric unit from group b, and a monomeric unit from group d.

In yet another example, the polymer of the present invention may comprise a monomeric unit from group a, a monomeric unit from group c, and a monomeric unit from group d.

In another example, the polymer of the present invention may comprise a monomeric unit from group b, a monomeric unit from group c, and a monomeric unit from group d.

In even yet another example, the polymer of the present invention may comprise a monomeric unit from group a, a monomeric unit from group b, a monomeric unit from group c and a monomeric unit from group d.

In one example, when present in the polymer, the monomeric unit from group b and the monomeric unit from group c are present in the polymer at a molar ratio of from about 3:1 to 1:3 and/or from about 2:1 to 1:2 and/or from about 1.3:1 to 1:1.3 and/or about 1:1 or less or about 1:1 or more.

In another example, when present in the polymer, the monomeric unit from group b and the monomeric unit from group d are present in the polymer at a molar ratio of from about 3:1 to 1:3 and/or from about 2:1 to 1:2 and/or from about 1.3:1 to 1:1.3 and/or about 1:1 or less or about 1:1 or more.

In another example, when present in the polymer, the monomeric unit from group c and the monomeric unit from group d are present in the polymer at a molar ratio of from about 3:1 to 1:3 and/or from about 2:1 to 1:2 and/or from about 1.3:1 to 1:1.3 and/or about 1:1 or less or about 1:1 or more.

In still another example, the polymer comprises a monomeric unit from group a and a monomeric unit from group c. For example, the polymer may comprise an acrylamide monomeric unit and a quaternary ammonium monomeric unit. The quaternary monomeric unit may be selected from the group consisting of: monoquaternary ammonium monomeric units, diquaternary ammonium monomeric units, and triquaternary ammonium monomeric units. In one example, the polymer may comprise at least 69.9% wt of the monomeric unit from group a and no more than 30.1% wt of the monomeric unit from group c.

In still another example, the polymer comprises a monomeric unit from group a and a monomeric unit from group b. For example, the polymer may comprise an acrylamide monomeric unit and an acrylic acid monomeric unit. In one example, the polymer may comprise at least 69.9% wt of the monomeric unit from group a and no more than 30.1% wt of the monomeric unit from group b.

In yet another example, the polymer comprises a monomeric unit from group b and a monomeric unit from group c. For example, the polymer may comprise an anionic monomeric unit derived from an anionic monomer selected from the group consisting of: acrylic acid, methacrylic acid, 2-acrylamido-2-methylpropane sulfonic acid, carboxyethyl acrylate, and mixtures thereof and a quaternary ammonium monomeric unit. The quaternary ammonium monomeric unit may be derived from a quaternary monomer selected from the group consisting of: monoquaternary ammonium monomeric units, diquaternary ammonium monomeric units, triquaternary ammonium monomeric units, and mixtures thereof. In one example, the polymer comprises an anionic monomeric unit derived from acrylic acid and a quaternary ammonium monomeric unit derived from MAPTAC. In one example, the polymer may comprise no more than 25% wt of the monomeric unit from group b and no more than 75% wt of the monomeric unit from group c.

In even yet another example, the polymer comprises a monomeric unit from group a and a monomeric unit from group b and a monomer unit from group c. For example, the polymer may comprise an acrylamide monomeric unit, and an anionic monomeric unit derived from an anionic monomer selected from the group consisting of: acrylic acid, methacrylic acid, 2-acrylamido-2-methylpropane sulfonic acid, carboxyethyl acrylate, and mixtures thereof and a quaternary ammonium monomeric unit. The quaternary ammonium monomeric unit may be derived from a quaternary monomer selected from the group consisting of: monoquaternary ammonium monomeric units, diquaternary ammonium monomeric units, triquaternary ammonium monomeric units, and mixtures thereof. In one example, the polymer comprises a nonionic monomeric unit derived from acrylamide, an anionic monomeric unit derived from acrylic acid, and a cationic monomeric unit derived from MAPTAC. In another example, the polymer comprises a nonionic monomeric unit derived from acrylamide, an anionic monomeric unit derived from acrylic acid, and a cationic monomeric unit derived from DADMAC. In still another example, the polymer comprises a nonionic monomeric unit derived from acrylamide, an anionic monomeric unit derived from acrylic acid, and a cationic monomeric unit derived from TQ. In another example, the polymer comprises a nonionic monomeric unit derived from acrylamide, an anionic monomeric unit derived from CEA, and a cationic monomeric unit derived from MAPTAC. In still another example, the polymer comprises a nonionic monomeric unit derived from acrylamide, an anionic monomeric unit derived from AMPS, and a cationic monomeric unit derived from MAPTAC. In one example, the polymer may comprise at least 69.9% wt of the monomeric unit from group a and no more than 30.1% wt combined of the monomeric units from groups b and c. In another example, the polymer may comprise from about 70% to about 99.5% wt of the monomeric unit from group a, from 0.1% to about 30% wt of the monomeric unit from group b, and from about 0.1% to about 30% wt of the monomeric unit from group c. In still another example, the polymer may comprise from about 70% to about 99.5% wt of the monomeric unit from group a and from about 0.5% to 30% wt combined of the monomeric units from groups b and c.

In even still yet another example, the polymer comprises a monomeric unit from group a and a monomeric unit from group c and a monomer unit from group d. For example, the polymer may comprise an acrylamide monomeric unit, a quaternary ammonium monomeric unit, and a zwitterionic monomeric unit selected from the group consisting of: CZ, SZ, and mixtures thereof. The quaternary ammonium monomeric unit may be derived from a quaternary monomer selected from the group consisting of: monoquaternary ammonium monomeric units, diquaternary ammonium monomeric units, triquaternary ammonium monomeric units, and mixtures thereof. In one example, the polymer comprises a nonionic monomeric unit derived from acrylamide, a cationic monomeric unit derived from MAPTAC, and a zwitterionic monomeric unit derived from CZ. In another example, the polymer comprises a nonionic monomeric unit derived from acrylamide, a cationic monomeric unit derived from MAPTAC, and a zwitterionic monomeric unit derived from SZ. In one example, the polymer may comprise at least 69.9% wt of the monomeric unit from group a and no more than 30.1% wt combined of the monomeric units from groups c and d. In another example, the polymer may comprise from about 70% to about 99.5% wt of the monomeric unit from group a, from 0.1% to about 30% wt of the monomeric unit from group c, and from about 0.1% to about 30% wt of the monomeric unit from group d. In still another example, the polymer may comprise from about 70% to about 99.5% wt of the monomeric unit from group a and from about 0.5% to 30% wt combined of the monomeric units from groups c and d.

In even yet another example, the polymer comprises a monomeric unit from group a and a monomeric unit from group b and a monomer unit from group d. For example, the polymer may comprise an acrylamide monomeric unit, and an anionic monomeric unit derived from an anionic monomer selected from the group consisting of: acrylic acid, methacrylic acid, 2-acrylamido-2-methylpropane sulfonic acid, carboxyethyl acrylate, and mixtures thereof and a zwitterionic monomeric unit selected from the group consisting of: CZ, SZ, and mixtures thereof. In one example, the polymer comprises a nonionic monomeric unit derived from acrylamide, an anionic monomeric unit derived from acrylic acid, and zwitterionic monomeric unit derived from CZ. In another example, the polymer comprises a nonionic monomeric unit derived from acrylamide, an anionic monomeric unit derived from acrylic acid, and a zwitterionic monomeric unit derived from SZ. In one example, the polymer may comprise at least 69.9% wt of the monomeric unit from group a and no more than 30.1% wt combined of the monomeric units from groups b and d. In another example, the polymer may comprise from about 70% to about 99.5% wt of the monomeric unit from group a, from 0.1% to about 30% wt of the monomeric unit from group b, and from about 0.1% to about 30% wt of the monomeric unit from group d. In still another example, the polymer may comprise from about 70% to about 99.5% wt of the monomeric unit from group a and from about 0.5% to 30% wt combined of the monomeric units from groups b and d.

In even yet another example, the polymer comprises a monomeric unit from group a and a monomeric unit from group d. For example, the polymer may comprise an acrylamide monomeric unit, and a zwitterionic monomeric unit selected from the group consisting of: CZ, SZ, and mixtures thereof. In one example, the polymer comprises a nonionic monomeric unit derived from acrylamide and zwitterionic monomeric unit derived from CZ. In another example, the polymer comprises a nonionic monomeric unit derived from acrylamide and a zwitterionic monomeric unit derived from SZ. In one example, the polymer may comprise at least 69.9% wt of the monomeric unit from group a and no more than 30.1% wt of the monomeric unit from group d. In another example, the polymer may comprise from about 70% to about 99.5% wt of the monomeric unit from group a, from 0.5% to about 30% wt of the monomeric unit from group d.

In one example, the polymer of the present invention comprises a nonionic hydrophilic monomeric unit. Non-limiting examples of suitable hydrophilic monomeric units are derived from nonionic hydrophilic monomers selected from the group consisting of: hydroxyalkyl esters of $\alpha,\beta$-ethylenically unsaturated acids, $\alpha,\beta$-ethylenically unsaturated amides, $\alpha,\beta$-ethylenically unsaturated monoalkyl amides, $\alpha,\beta$-ethylenically unsaturated dialkyl amides, $\alpha,\beta$-ethylenically unsaturated monomers bearing a water-soluble polyoxyalkylene segment of the poly(ethylene oxide) type, $\alpha,\beta$-ethylenically unsaturated monomers which are precursors of hydrophilic units or segments, vinylpyrrolidones, $\alpha,\beta$-ethylenically unsaturated monomers of the ureido type, and mixtures thereof. In one example, the nonionic hydrophilic monomeric unit is derived from acrylamide.

In another example, the polymer of the present invention comprises a nonionic hydrophobic monomeric unit. Non-limiting examples of suitable nonionic hydrophobic monomeric units are derived from nonionic hydrophobic monomers selected from the group consisting of: vinylaromatic monomers, vinyl halides, vinylidene halides, $C_1$-$C_{12}$ alkylesters of $\alpha,\beta$-monoethylenically unsaturated acids, vinyl esters of saturated carboxylic acids, allyl esters of saturated carboxylic acids, $\alpha,\beta$-monoethylenically unsaturated nitriles containing from 3 to 12 carbon atoms, $\alpha$-olefins, conjugated dienes, and mixtures thereof.

In one example, the polymer comprises an anionic monomeric unit. Non-limiting examples of suitable anionic monomeric units are derived from anionic monomers selected from the group consisting of: monomers having at least one carboxylic function, for instance $\alpha,\beta$-ethylenically unsaturated carboxylic acids or the corresponding anhydrides, monomers that are precursors of carboxylate functions, monomers having at least one sulfate or sulfonate function, monomers having at least one phosphonate or phosphate function, esters of ethylenically unsaturated phosphates, and mixtures thereof. In one example, the anionic monomeric unit is derived from an anionic monomer selected from the group consisting of: acrylic acid, methacrylic acid, 2-acrylamido-2-methylpropane sulfonic acid, carboxyethyl acrylate, and mixtures thereof.

In one example, the polymer comprises a cationic monomeric unit. Non-limiting examples of suitable cationic monomeric units are derived from cationic monomers selected from the group consisting of: acryloyl- or acryloyloxyammonium monomers, 1-ethyl-2-vinylpyridinium or 1-ethyl-4-vinylpyridinium bromide, chloride or methyl sulfate, N,N-dialkyldiallylamine monomers, polyquaternary monomers, N,N-(dialkylamino-$\omega$-alkyl)amides of $\alpha,\beta$-monoethylenically unsaturated carboxylic acids, $\alpha,\beta$-monoethylenically unsaturated amino esters, vinylpyridines, vinylamine, vinylimidazolines, monomers that are precursors of amine functions which give rise to primary amine functions by simple acid or base hydrolysis, and mixtures thereof. In one example, the cationic monomeric unit is derived from MAPTAC. In another example, the cationic monomeric unit is derived from DADMAC. In still another example, the cationic monomeric unit is derived from 2-hydroxy-$N^1$-(3-(2((3-methacrylamidopropyl)dimethylamino)-acetamido)propyl)-$N^1,N^1,N^3,N^3,N^3$-pentamethylpropane-1,3-diaminium chloride.

In one example, the soil capture agents are water-soluble.

The soil capture agents may be made by any suitable process known in the art. For example, the soil capture agent polymers may be made by radical polymerization.

The soil capture agent polymers of the present invention can be made by a wide variety of techniques, including bulk, solution, emulsion, or suspension polymerization. Polymerization methods and techniques for polymerization are described generally in Encyclopedia of Polymer Science and Technology, Interscience Publishers (New York), Vol. 7, pp. 361-431 (1967), and Kirk-Othmer Encyclopedia of Chemical Technology, 3rd edition, Vol 18, pp. 740-744, John Wiley & Sons (New York), 1982, both incorporated by reference herein. See also Sorenson, W. P. and Campbell, T. W., Preparative Methods of Polymer Chemistry. 2nd edition, Interscience Publishers (New York), 1968, pp. 248-251, incorporated by reference herein, for general reaction techniques suitable for the present invention. In one example, the polymers are made by free radical copolymerization, using water soluble initiators. Suitable free radical initiators include, but are not limited to, thermal initiators, redox couples, and photochemical initiators. Redox and photochemical initiators may be used for polymerization processes initiated at temperatures below about 30° C. (86° F.). Such initiators are described generally in Kirk-Othmer Encyclopedia of Chemical Technology, 3rd edition, John Wiley & Sons (New York), Vol. 13, pp. 355-373 (1981), incorporated by reference herein. Typical water soluble initiators that can provide radicals at 30° C. or below include redox couples, such as potassium persulfate/silver nitrate, and ascorbic acid/hydrogen peroxide. In one example, the method utilizes thermal initiators in polymerization processes conducted above 40° C. (104° F.). Water soluble initiators that can provide radicals at 40° C. (104° F.) or higher can be used. These include, but are not limited to, hydrogen peroxide, ammonium persulfate, and 2,2'-azobis (2-amidinopropane)dihydrochloride. In one example, water soluble starting monomers are polymerized in an aqueous alcohol solvent at 60° C. (140° F.) using 2,2'-azobis(2-amidinopropane)dihydrochloride as the initiator. The solvent should typically contain at least about 10% by volume, of alcohol in order to prevent the polymerization reaction medium from gelling. Suitable alcohols for use in such reaction include low molecular weight alcohols such as, but not limited to, methanol, ethanol, isopropanol, and butanol.

Another technique is a solution polymerization as described in U.S. Pat. No. 3,317,370, Kekish, issued May 2, 1967 and U.S. Pat. No. 3,410,828, Kekish, issued Nov. 12, 1968, both incorporated herein by reference. According to such process, the acrolein, or other aldehydic monomer, is copolymerized with a non-nucleophilic, water soluble, nitrogen-heterocyclic polymerizable monomer and a redox initiator system. The copolymer is then made cationic by reacting the copolymer with a water soluble amine or amine quaternary. Amines, including amine quaternaries, that are useful include, but are not limited to, primary, secondary, and tertiary amines such as ethylene diamine, diethylene triamine, triethylene tetramine, tetraethylene pentamine, or partial or fully quaternized derivatives of any of the foregoing, hydrazides and quaternaries thereof such as betaine hydrazide chloride, N—N-dimethylglycine hydrazide, unsymmetrical dimethyl hydrazides, polymers, such as those formed by reaction of urea and polyalkylene polyamines, guanidines, biguanides, guanylureas, mono and polyhydroxy polyamines and quaternaries thereof, etc. When using this emulsion copolymerization technique, it will be necessary to control molecular weight to within the ranges provided herein.

Test Methods

Consumption Rate Test

To measure the Consumption Rate of a laminate cleaning implement, use a rotary tumbler (Lortone, Inc., Seattle, Wash., USA model 33B or equivalent) with 4 in. diameter by 4 in. deep cylindrical rubber housing having 825 cc internal volume. The housing revolves on the tumbler at 43 rpm. Obtain a supply of tap water at about 7.5 grains water hardness and conductivity between 100 to not more than 400 microSemens per centimeter (µS/cm) and heat in a reservoir beaker to 45° C. Maintain the water supply at the target temperature within 1 degree for the test duration. Add 200.0 g water from the reservoir to the housing. Weigh a laminate cleaning implement to obtain the initial weight, and add the laminate cleaning implement to the housing. Seal the housing with its accompanying watertight lid and place the sealed housing onto the rotary tumbler for exactly 3 minutes. Remove the housing, remove the housing lid, and retrieve the laminate cleaning implement. Stir the remaining water in the housing for a few seconds and measure its conductivity and temperature using a Mettler Toledo Seven multimeter with InLab 740 probe or equivalent. Dry the laminate cleaning implement surface by pressing, not rubbing, using paper towels with light hand pressure for about 30 seconds, until it is dry to the touch and transfers no more visible water to a dry paper towel using the same pressure at any point on its surface or edges. If the laminate cleaning implement transfers partially dissolved or dissolving components in addition to liquid water, for example if the substrate is a composition similar to conventional bar soap it may transfer paste-like material, the transferred components are to be removed and the laminate cleaning implement is considered dry when visible transfer is no longer evident. Weigh the laminate cleaning implement.

Empty and rinse the housing in hot tap water and dry it to complete 1 cycle. Repeat the cycle with the same laminate cleaning implement 4 more times for a total of 5 cycles. Measure the conductivity of the water reservoir at 30° C., 35° C., 40° C., and 45° C. Using a new laminate cleaning implement that is the same as the first one, prepare a 1% solution by removing 1.00 g of its substrate and adding it to 99.00 grams of water from the reservoir. Dissolve the substrate completely, using agitation and heat as necessary. Measure conductivity of the 1% solution at the same 4 temperatures. Prepare a 2% solution in the same way (2.00 grams substrate in 98.00 grams water), and measure its conductivity at the same 4 temperatures. Regress the conductivity vs. temperature results for each solution (0%, 1%, and 2%) and obtain the algebraic expressions for each.

For each conductivity-temperature datum for the water in the housing obtained during the each cycle, calculate the regressed conductivity for the 0%, 1% and 2% solutions at the temperature measured by the InLab 470 probe for each cycle. Execute a second set of linear regressions for each temperature obtained in the cycles using the solution concentrations (0%, 1% and 2%) as the y (output) and the regressed conductivity values as x (input). Use this second regression at each temperature obtained in each cycle with its paired conductivity value obtained as the input value for x to obtain y, which is the amount of solids of the laminate cleaning implement dissolved for each cycle. Add the dissolved solids for the 5 cycles and divide by 5 to obtain the Average Dissolved Solids. Multiply the value by 1.67 to obtain the consumption rate of the laminate cleaning implement.

Dissolution Test Method

Apparatus and Materials:
  600 mL Beaker
  Magnetic Stirrer (Labline Model No. 1250 or equivalent)
  Magnetic Stirring Rod (5 cm)
  Thermometer (1 to 100° C.+/−1° C.)
  Template, Stainless Steel (3.8 cm×3.2 cm)
  Timer (0-300 seconds, accurate to the nearest second)
  35 mm Slide Mount having an open area of 3.8 cm×3.2 cm (commercially available from Polaroid Corporation)
  35 mm Slide Mount Holder
  City of Cincinnati Water or equivalent having the following properties: Total Hardness=155 mg/L as CaCO3; Calcium content=33.2 mg/L; Magnesium content=17.5 mg/L; Phosphate content=0.0462

Sample Preparation:
1. Cut 3 test samples from a substrate to be tested ("sample") using the template to ensure that the sample fits within the 35 mm slide mount with open area dimensions 24×36 mm (i.e. 3.8 cm×3.2 cm specimen). Cut the samples from areas of the substrate equally spaced along the transverse direction of the dissolvable film substrate or the dissolvable filament substrate. As one of ordinary skill in the art would know, the basis weight of the sample is measured and the sample weight is determined by utilizing the open area dimensions.
2. Lock each of the 3 samples in a separate 35 mm slide mount.
3. Place magnetic stirring rod into the 600 mL Beaker.
4. Obtain 500 mL or greater of Cincinnati city water and measure water temperature with thermometer and, if necessary, adjust the temperature of the water to maintain it at the testing temperature; namely, 5° C. Once the water temperature is at 5° C., fill the 600 mL beaker with 500 mL of the water.
5. Next, place the beaker on the magnetic stirrer. Turn the stirrer on, and adjust stir speed until a vortex develops in the water and the bottom of the vortex is at the 400 mL mark on the 600 mL beaker.
6. Secure the 35 mm slide mount with sample locked therein in a holder designed to lower the 35 mm slide mount into the water in the beaker, for example an alligator clamp of a 35 mm slide mount holder designed to position the 35 mm slide mount into the water present in the 600 mL beaker. The 35 mm slide mount is held by the alligator clamp in the middle of one long end of the 35 mm slide mount such that the long ends of the 35 mm slide mount are parallel to the surface of the water present in the 600 mL beaker. This set up will position the film or nonwoven surface perpendicular to the flow of the water. A slightly modified example of an arrangement of a 35 mm slide mount and slide mount holder are shown in FIGS. 1-3 of U.S. Pat. No. 6,787, 512.

7. In one motion, the 35 mm slide mount holder, which positions the 35 mm slide mount above the center of the water in the beaker, is dropped resulting in the 35 mm slide mount becoming submerged in the water sufficiently such that the water contacts the entire exposed surface area of the film or nonwoven sample locked in the 35 mm slide mount. As soon as the water contacts the entire exposed surface area of the film or nonwoven start the timer. Disintegration occurs when the film or nonwoven breaks apart. When all of the visible film or nonwoven is released from the slide mount, raise the 35 mm slide mount out of the water while continuing to monitor the water for undissolved film or nonwoven fragments. Dissolution occurs when all film or nonwoven fragments are no longer visible in the water.

8. Three replicates of each sample are run.

9. Each disintegration and dissolution time is normalized by weight of the sample to obtain values of the disintegration and dissolution times per g of sample tested, which is in units of seconds/gram of sample (s/g). The average disintegration and dissolution times per g of sample tested of the three replicates are recorded. As one of ordinary skill in the art would know, the disintegration time and dissolution time for each sample is also recorded.

Charge Density Test Method

The charge density of a polymer, such as a soil adsorption polymer, can be determined by using a Mutek PCD-04 Particle Charge Detector available from BTG, or equivalent instrument. The following guidelines provided by BTG are used.

Start with a 0.1% solution (0.1 g polymer+99.9 g deionized water) (sample). Depending on the titrant consumption increase or decrease polymer content if needed. Solution pH is adjusted prior to final dilution as charge density of many polymers and/or additives is dependent upon solution pH. A pH of 4.5 is used here.

1. Place 20 mL of sample in the PCD measuring cell and insert piston.
2. Put the measuring cell with piston and sample in the PCD, the electrodes are facing the rear. Slide the cell along the guide until it touches the rear.
3. Pull piston upwards and turn it counter-clock-wise to lock the piston in place.
4. Switch on the motor. The streaming potential is shown on the touch panel. Wait 2 minutes until the signal is stable.
5. Use an oppositely charged titrant (for example for a cationic sample having a positive streaming potential: use an anionic titrant). Titrants are available from BTG consisting of 0.001N PVSK or 0.001N PolyDADMAC.
6. An automatic titrator available from BTG is utilized. After selecting the proper titrant, set the titrator to rinse the tubing by dispensing 10 mL insuring that all air bubbles have been purged.
7. Place tubing tip below the surface of the sample and start titration. The automatic titrator is set to stop automatically when the potential reaches 0 mV.
8. Record consumption of titrant, ideally, the consumption of titrant should be 0.2 mL to 10 mL; otherwise decrease or increase polymer content.
9. Repeat titration of a second 20 mL aliquot of the polymer sample.
10. Calculate charge demand (solution) or charge demand (solids);

$$\text{Charge demand (eq/L)} = \frac{V \text{ titrant used (L)} \times \text{Conc. of titrant in Normality (eq/L)}}{\text{Volume of sample titrated (L)}}$$

$$\text{Charge demand (eq/g)} = \frac{V \text{ titrant used (L)} \times \text{Conc. of titrant in Normality (eq/L)}}{\text{Wt. solids of the sample or its active substance (g)}}$$

The charge demand (charge density) of a polymer is reported in meq/g units.

Gas Pycnometry Method

The Percent Open Cell Content is measured via gas pycnometry. Gas pycnometry is a common analytical technique that uses a gas displacement method to measure volume accurately. Inert gases, such as helium or nitrogen, are used as the displacement medium. The sample is sealed in the instrument compartment of known volume, the appropriate inert gas is admitted, and then expanded into another precision internal volume. The pressure before and after expansion is measured and used to compute the sample volume. Dividing this volume into the sample weight gives the gas displacement density.

The percentage of open cells can be determined by performing a test which uses Micromeritics® AccuPyc Pycnometer. The ASTM procedure D2856 describes 5 methods (A, B, C, D, and E) for determining the percent of open cells of foam materials.

For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the true volume as measured by the Accupyc. It is recommended that these measurements be conducted by Micromeretics® Analytical Services, Inc. (One Micromeritics Dr, Suite 200, Norcross, Ga. 30093). More information on this technique is available in "Analytical Methods in Fine particle Technology", by Clyde Orr and Paul Webb.

Specific Surface Area Method

The Specific Surface Area of a substrate that comprise an open cell foam is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the degassed sample+sample tube weight. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved.

Sample Preparation (Degassing): A sample not adequately cleaned of adsorbed contaminants will outgas during an analysis and some portion of the surface will be inaccessible to measurement. The purpose of degassing is to remove these adsorbed molecules from the surface of the sample prior to analysis. Adsorptive molecules must reach all parts of the surface for the true surface area to be revealed. Samples are prepared by heating the sample while simultaneously evacuating the sample tube.

For these experiments, the samples are outgassed under evacuation at room temperature overnight. Samples may then analyzed using an ASAP 2420 with krypton gas adsorption. Krypton gas is preferred over nitrogen gas as it has a saturation pressure approximately 1/300 that of nitrogen at liquid nitrogen temperature (krypton: 2.5 ton; nitrogen: 760 ton). Therefore, compared to nitrogen, there is in the free space above the sample 1/300 the number of krypton molecules present at the same relative pressure. Since the same number of krypton and nitrogen molecules are required to form a monolayer, this number represents a far greater proportion of the quantity dosed than in the case of nitrogen. These measurements can be conducted by Micromeretics® Analytical Services, Inc. (One Micromeritics Dr, Suite 200, Norcross, Ga. 30093). More information on this technique is available in "Analytical Methods in Fine particle Technology", by Clyde Orr and Paul Webb.

Water Content Test Method

The water (moisture) content present in a filament and/or fiber and/or substrate is measured using the following Water Content Test Method.

A substrate or portion thereof ("sample") is placed in a conditioned room at a temperature of 73° F.±4° F. (about 23° C.±2.2° C.) and a relative humidity of 50%±10% for at least 24 hours prior to testing. The weight of the sample is recorded when no further weight change is detected for at least a 5 minute period. Record this weight as the "equilibrium weight" of the sample. Next, place the sample in a drying oven for 24 hours at 70° C. with a relative humidity of about 4% to dry the sample. After the 24 hours of drying, immediately weigh the sample. Record this weight as the "dry weight" of the sample. The water (moisture) content of the sample is calculated as follows:

$$\% \text{ Water (moisture) in sample} = 100\% \times \frac{(\text{Equilibrium weight of sample} - \text{Dry weight of sample})}{\text{Dry weight of sample}}$$

The % Water (moisture) in sample for 3 replicates is averaged to give the reported % Water (moisture) in sample.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular examples of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A laminate cleaning implement comprising:
   a. a backing sheet;
   b. a dissolvable substrate comprising an active agent wherein upon exposure to conditions of intended use the active agent is released from the dissolvable substrate, wherein the dissolvable substrate comprises about 10% or less moisture by weight of the dissolvable substrate as measured according to the Water Content Test Method; and
   c. a facing sheet; wherein the backing sheet and the facing sheet are connected at a plurality of discrete bonding points to form a coherent laminate structure and wherein the dissolvable substrate is disposed between the backing sheet and the facing sheet.

2. The laminate cleaning implement of claim 1 wherein the dissolvable substrate is substantially displaced out of the plurality of bonding points.

3. The laminate cleaning implement of claim 1 wherein the facing sheet is a high loft batting material.

4. The laminate cleaning implement of claim 1 wherein the facing sheet comprises apertures.

5. The laminate cleaning composition of claim 1 wherein the backing sheet is water impermeable.

6. The laminate cleaning implement of claim 1 wherein the dissolvable substrate comprises a plurality of particles wherein the particles are substantially held into place by the coherent laminate structure.

7. The laminate cleaning implement of claim 1 wherein upon exposure to conditions of intended use the dissolvable substrate lathers.

8. The laminate cleaning implement of claim 1 wherein the cleaning implement has a consumption rate of about 3 g/use to about 30 g/use.

9. The laminate cleaning implement of claim 1 wherein the dissolvable substrate dissolves in less than about 60 seconds per gram.

10. The laminate cleaning implement of claim 1 wherein the dissolvable substrate is an open cell foam with a percent open cell content of from about 80% to about 100%.

11. The laminate cleaning implement of claim 1 wherein the dissolvable substrate is an open cell foam with a specific surface area of from about 0.03 $m^2/g$ to about 0.25 $m^2/g$.

12. The laminate cleaning implement of claim 1 wherein the dissolvable substrate is a dissolvable filament substrate comprising less than about 7% moisture.

13. The laminate cleaning implement of claim 1 wherein the laminate cleaning implement is an on-the-hand implement.

14. The laminate cleaning implement of claim 1 wherein the laminate cleaning implement is adapted to be affixed to an on-the-hand implement.

15. The laminate cleaning implement of claim 1 wherein the implement further comprises a usage indicator.

16. The laminate cleaning implement of claim 1 wherein the active agent is selected from the group consisting of conditioning agents, surfactants, skin cleansing agents, skin care agents, moisturizers, protectants, barrier materials, smoothing agents, lubricants, fabric softening agents, fabric care stain removal agents, soil release agents, dishwashing agents, hard surface cleansing agents, bleaching agents, carpet care agents, make-up removal agents, deposition aids, perfumes, odor absorbing agents, tooth care agents, ear care agents, and mixtures thereof.

17. The laminate cleaning implement according to claim 1 wherein the laminate cleaning implement further comprises a soil capture agent.

18. The laminate cleaning implement according to claim 17 wherein the soil capture agent is present on the facing sheet.

19. An on-the-hand implement comprising a bonded laminate comprising:
   a. a water impermeable backing sheet wherein the backing sheet is adapted to be in contact with a user's hand during use;
   b. a dissolvable substrate comprising an active agent wherein upon exposure to conditions of intended use the active agent is released from the dissolvable substrate, wherein the dissolvable substrate comprises about 10% or less moisture by weight of the dissolvable substrate as measured according to the Water Content Test Method; and
   c. a water permeable facing sheet;
      wherein the backing sheet and the facing sheet are connected at a plurality of discrete bonding points to form a coherent laminate structure and wherein the dissolvable substrate is disposed between the backing sheet and the facing sheet.

20. The on-the-hand implement of claim 19 wherein the implement does not cover the user's fingers during use.

21. The on-the-hand implement of claim 19 wherein the implement further comprises a usage indicator.

22. The on-the-hand implement according to claim 19 wherein the on-the-hand implement further comprises a soil capture agent.

23. The on-the-hand implement according to claim 22 wherein the soil capture agent is present on the facing sheet.

24. A laminate cleaning implement comprising (a) a facing sheet and (b) a dissolvable substrate comprising an active agent wherein upon exposure to conditions of intended use the active agent is released from the dissolvable substrate, wherein the dissolvable substrate comprises about 10% or less moisture by weight of the dissolvable substrate as measured according to the Water Content Test Method, wherein the facing sheet and dissolvable substrate are connected at a plurality of discrete bonding points to form a coherent laminate.

* * * * *